United States Patent
Axelson

(10) Patent No.: US 11,332,529 B2
(45) Date of Patent: May 17, 2022

(54) METHODS OF TREATING COLORECTAL CANCER

(71) Applicant: Bristol-Myers Squibb Company, Princeton, NJ (US)

(72) Inventor: Michael Axelson, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 59 days.

(21) Appl. No.: 16/306,290

(22) PCT Filed: Jun. 2, 2017

(86) PCT No.: PCT/US2017/035822
§ 371 (c)(1),
(2) Date: Nov. 30, 2018

(87) PCT Pub. No.: WO2017/210637
PCT Pub. Date: Dec. 7, 2017

(65) Prior Publication Data
US 2019/0153100 A1    May 23, 2019

Related U.S. Application Data

(60) Provisional application No. 62/345,662, filed on Jun. 3, 2016.

(51) Int. Cl.
*A61K 39/395* (2006.01)
*C07K 16/28* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *C07K 16/2827* (2013.01); *C07K 16/2878* (2013.01); *A61K 2039/507* (2013.01)

(58) Field of Classification Search
None
See application file for complete search history.

(56) References Cited

U.S. PATENT DOCUMENTS

| | | | |
|---|---|---|---|
| 5,977,318 A | 11/1999 | Linsley et al. | |
| 6,051,227 A | 4/2000 | Allison et al. | |
| 6,682,736 B1 | 1/2004 | Hanson et al. | |
| 6,808,710 B1 | 10/2004 | Wood et al. | |
| 6,984,720 B1 | 1/2006 | Korman et al. | |
| 7,034,121 B2 | 4/2006 | Carreno et al. | |
| 7,488,802 B2 | 2/2009 | Collins et al. | |
| 7,595,048 B2 | 9/2009 | Honjo et al. | |
| 7,605,238 B2 | 10/2009 | Korman et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,609,089 B2 | 12/2013 | Langermann et al. | |
| 8,728,474 B2 | 2/2014 | Honjo et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,212,224 B2 | 12/2015 | Cogswell et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,856,320 B2 | 2/2018 | Cogswell et al. | |
| 10,072,082 B2 | 9/2018 | Cogswell et al. | |
| 10,138,299 B2 | 11/2018 | Cogswell et al. | |
| 2006/0110383 A1 | 5/2006 | Honjo et al. | |
| 2009/0217401 A1 | 8/2009 | Korman et al. | |
| 2009/0297518 A1 | 12/2009 | Honjo et al. | |

(Continued)

FOREIGN PATENT DOCUMENTS

| | | |
|---|---|---|
| CN | 110505882 A | 11/2019 |
| WO | WO-2003072822 A2 | 9/2003 |

(Continued)

OTHER PUBLICATIONS

Anonymous: "An Investigational Immuno-therapy Study of Nivolumab. and Nivolumab in Combination With Other Anti-cancer Drugs, in Colon Cancer That Has Come Back or Has Spread—Full Text View—Clinical Trials.gov", Dec. 18, 2013 (Dec. 18, 2013). XP055390376. Retrieved from the Internet: URL:https://clinicaltrials.gov/ct2/show/NCT02060188 [retrieved on Apr. 11, 2019].

Anonymous: "Phase 2 Study of MK-3475 in Patients With Microsatellite Unstable (MSI) Tumors—Full Text View Clinical Trials. gov " Jun. 10, 2013 (Jun. 10, 2013). XP055390377. Retrieved from the Internet: URL:https://clinicaltrials.gov/ct2/show/NCT01876511 [retrieved on Apr. 11, 2019].

Ansell, S., et al., "Nivolumab in Patients (Pts) With Relapsed or Refractory Classical Hodgkin Lymphoma (R/R cHL): Clinical Outcomes From Extended Follow-up of a Phase 1 Study (CA209-039)," Blood 126(23):583, American Society of Hematology, United States (Dec. 3, 2015).

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

This disclosure provides methods for treating a tumor derived from a colorectal cancer exhibiting a high degree of microsatellite instability in a subject comprising administering to the subject an anti-PD-1 antibody. In some embodiments, the method further comprises administering an anti-CTLA-4 antibody. In some embodiments, the colorectal cancer is rectal cancer, colon cancer, or any combination thereof.

18 Claims, 12 Drawing Sheets

(56) References Cited

U.S. PATENT DOCUMENTS

| | | |
|---|---|---|
| 2011/0081341 A1 | 4/2011 | Honjo et al. |
| 2012/0263677 A1 | 10/2012 | Eagle et al. |
| 2013/0017199 A1 | 1/2013 | Langermann et al. |
| 2013/0133091 A1 | 5/2013 | Korman et al. |
| 2013/0309250 A1 | 11/2013 | Cogswell et al. |
| 2014/0212422 A1 | 7/2014 | Korman et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341917 A1 | 11/2014 | Nastri et al. |
| 2014/0348743 A1 | 11/2014 | Korman et al. |
| 2014/0356353 A1 | 12/2014 | Queva et al. |
| 2015/0079109 A1 | 3/2015 | Li et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2016/0090417 A1 | 3/2016 | Cogswell et al. |
| 2016/0158355 A1 | 6/2016 | Honjo et al. |
| 2016/0158356 A1 | 6/2016 | Honjo et al. |
| 2017/0051060 A1 | 2/2017 | Honjo et al. |
| 2017/0088615 A1 | 3/2017 | Korman et al. |
| 2018/0273624 A1 | 9/2018 | Cogswell et al. |
| 2018/0282414 A1 | 10/2018 | Cogswell et al. |
| 2018/0282413 A1 | 11/2018 | Cogswell et al. |
| 2018/0312590 A1 | 11/2018 | Cogswell et al. |
| 2018/0319887 A1 | 11/2018 | Cogswell et al. |
| 2019/0092863 A1 | 3/2019 | Cogswell et al. |
| 2019/0100589 A1 | 4/2019 | Cogswell et al. |
| 2019/0100590 A1 | 4/2019 | Cogswell et al. |

FOREIGN PATENT DOCUMENTS

| | | |
|---|---|---|
| WO | WO-2004004771 A1 | 1/2004 |
| WO | WO-2005021743 A1 | 3/2005 |
| WO | WO-2007113648 A2 | 10/2007 |
| WO | WO-2012122444 A1 | 9/2012 |
| WO | WO-2012145493 A1 | 10/2012 |
| WO | WO-2013004618 A1 | 1/2013 |
| WO | WO-2013173223 A1 | 11/2013 |
| WO | WO-2014179664 A2 | 11/2014 |
| WO | WO-2014194302 A2 | 12/2014 |
| WO | WO-2015085847 A1 | 6/2015 |
| WO | WO-2015112800 A1 | 7/2015 |
| WO | WO-2015112900 A1 | 7/2015 |
| WO | WO-2016077553 A1 | 5/2016 |
| WO | WO-2016149201 A2 | 9/2016 |
| WO | WO-2006121168 A1 | 11/2016 |
| WO | WO-2016197067 A1 | 12/2016 |

OTHER PUBLICATIONS

Drake, "Safety, Durable Clinical Benefit, and Remission Resulting from Nivolumanb (Anti-PD-1; BMS-936558; ONO-4538) in a Phase 1 Trial in Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," BJU International 112 (Suppl 3):1-17, Blackwell Science, England (Nov. 2013).

Dudley, J.C., et al., "Microsatellite Instability as a Biomarker for PD-1 Blockade," Clinical Cancer Research 22(4):813-820, The Association, United States (Feb. 2016).

Duraiswamy, J., et al., "Dual Blockade of PD-1 and CTLA-4 Combined With Tumor Vaccine Effectively Restores T-cell Rejection Function in Tumors," Cancer Research 73(12):3591-3603, American Association for Cancer Research, United States (Jun. 2013).

GenBank, "Cytotoxic T-lymphocyte-associated protein 4 [*Homo sapiens*]," Accession No. AAB59385.1, accessed on https://www.ncbi.nlm.nih.gov/protein/AAB59385, Nov. 1, 1994.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.

Hamid, O. and Carvajal, R.D., "Anti-programmed Death-1 and Anti-programmed Death-ligand 1 Antibodies in Cancer Therapy," Expert Opinion on Biological Therapy 13(6):847-861, Taylor & Francis, England (Jun. 2013).

Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).

Hodi, F.S., et al., "Improved Survival with Ipilimumab in Patients with Metastatic Melanoma," The New England Journal of Medicine 363(8):711-723, Massachusetts Medical Society, United States (Aug. 2010).

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Kroemer, G., et al., "Colorectal Cancer: the First Neoplasia Found to Be Under Immunosurveillance and the Last One to Respond to Immunotherapy?," Oncoimmunology 4(7):e1058597, Taylor & Francis, United States (Jun. 2015).

Le, D.T., et al., "PD-1 Blockade in Tumors with Mismatch-Repair Deficiency," The New England Journal of Medicine 372(26):2509-2520, Massachusetts Medical Society, United States (Jun. 2015).

Li, S.K.H and Martin, A, "Mismatch Repair and Colon Cancer: Mechanisms and Therapies Explored," Trends in Molecular Medicine 22(4):274-289, Elsevier Science Ltd, England (Apr. 2016).

Llosa, N.J., et al., "The Vigorous Immune Microenvironment of Microsatellite Instable Colon Cancer is Balanced by Multiple Counter-inhibitory Checkpoints," Cancer Discovery 5(1):43-51, American Association for Cancer Research, United States (Jan. 2015).

McDermott, D.F., and Atkins, M.B., "PD-1 as a Potential Target in Cancer Therapy," Cancer Medicine 2(5):662-673, John Wiley & Sons Ltd., United States (Oct. 2013).

National Cancer Institute, Colorectal Cancer, available at: http://www.cancer.gov/types/colorectal, last visited Feb. 14, 2017, 6 pages . . . .

NCCN Guidelines® (2014), available at http://www.nccn.org/professionals/physician_gls/f_guidelines.asp, last accessed May 14, 2014, 4 pages.

NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, anti-PD-1 monoclonal antibody MED10680, accessed on Dec. 1, 2016, retrieved from the Internet URL: https://www.cancer.gov/publications/dictionaries/cancer-drug?cdrid=756047.

NCI Drug Dictionary, pembrolizumab, accessed on Dec. 1, 2016, retrieved from the Internet URL: https://www.cancer.gov/drugdictionary?cancer-drug?cdrid=695789, 3 pages.

Pawlik, T.M., et al., "Colorectal Carcinogenesis: MSI-H Versus MSI-L," Disease Markers 20(4-5):199-206, Hindawi Pub. Corp, United States (2004).

International Search report and Written Opinion for Application No. PCT/US2017/035822, dated Aug. 1, 2017, 14 pages.

Postow, M.A, "Managing Immune Checkpoint-blocking Antibody Side Effects," American Society of Clinical Oncology—Educational Book 35(1):76-83, American Society of Clinical Oncology, United States (2015).

Rosenbaum, M.W., et al., "PD-L1 Expression in Colorectal Cancer is Associated With Microsatellite Instability, BRAF Mutation, Medullary Morphology and Cytotoxic Tumor-infiltrating Lymphocytes," Modern Pathology 29(9):1104-1112, Nature Publishing Group, United States (Sep. 2016).

(56) References Cited

OTHER PUBLICATIONS

Selby, M.J., et al., "Preclinical Development of Ipilimumab and Nivolumab Combination Immunotherapy: Mouse Tumor Models, In Vitro Functional Studies, and Cynomolgus Macaque Toxicology," PLoS One 11(9):e0161779, Public Library of Science, United States (Sep. 2016).

Sjoblom, T., et al., "The Consensus Coding Sequences of Human Breast and Colorectal Cancers," Science 314(5797):268-274, American Association for the Advancement of Science, United States (Oct. 2006).

Overman M.J., et al., "479P—Nivolumab ± ipilimumab treatment (Tx) efficacy, safety, and biomarkers in patients (Pts) with metastatic colorectal cancer (mCRC) with and without High Microsatellite Instability(MSI-H): results from the CheckMate-142 study," Annals of Oncology, 27(6):149-206, (Oct. 2016).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Topalian, S.L., et al., "Targeting the PD-1/67-H1(PD-L1) Pathway to Activate Anti-tumor Immunity," Current Opinion in Immunology 24(2):207-212, Elsevier, England (Apr. 2012).

Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

Zumwalt, T.J., et al., "Immunotherapy of Metastatic Colorectal Cancer: Prevailing Challenges and New Perspectives," Current Colorectal Cancer Reports 11(3):125-140, (Jun. 2015).

Anonymous: "An Investigational Immuno-therapy Study of Nivolumab. and Nivolumab in Combination With Other Anti-cancer Drugs, in Colon Cancer That Has Come Back or Has Spread—Full Text View—Clinical Trials.gov". Retrieved from the Internet: URL: ttps://clinicaltrials.gov/ct2/history/NCT02060188?V_50=View#StudyPageTop [retrieved on Jun. 23, 2021], 9 pages.

Anonymous: "A Study of Nivolumab and Nivolumab Plus Ipilimumab in Recurrent and Metastatic Colon Cancer (CheckMate 142)". Retrieved from the Internet: URL: https://clinicaltrials.gov/ct2/history/NCT02060188?V_17=View#StudyPageTop [retrieved on Aug. 30, 2021], 9 pages.

Anonymous: "Phase 2 Study of MK-3475 in Patients with Microsatellite Unstable (MSI) Tumors—Full Text Clinical Trials. gov" Sep. 24, 2013 (Sep. 24, 2013). Retrieved from the Internet: URL: https://clinicaltrials.gov/ct2/show/NCT01876511 [retrieved on Aug. 30, 2021], 4 pages.

Bacher, J.W., et al., "Development of a flourescent multiplex assay for detection of MSI-High tumors," Dis Markers 20(4-5):237-250, IOS Press, United States (2004).

Durie, N. et al., "Retrospective review of colorectal cancer specimens in individuals younger than age 50 for microsattelite instability testing and DNA mismatch repair enzyme expression," Journal of Clinical Oncology 29(4):392-392, American Society of Clinical Oncology, United States (2011).

Eroglu, Z., et al., "Checkpoint Inhibition of PD-1: The Promise of Pembrolizumab (MK-3475) and Beyond," Perzonalied Medicine in Oncology: 13 pages, The Lynx Group, United States (2014).

Gatalica, Z., et al., "Programmed cell death 1 (PD-1) and its ligand (PD-L1) in common cancers and their correlation with molecular cancer type," Cancer Epidemiol Biomarkers Prev 23(12):2965-2970, American Association of Cancer Research, United States (2014).

Le, D., et al., "Phase 2 stude of programmed death-1 antibody (anti-PD-1, MK-3475) in patients with microsatellite unstable (MSI) tumors," Journal of Clinical Oncology, 32(15): 4 pages, American Society of Clinical Oncology Journal, United States (2014).

Lipson, E.J., et al., "Durable Cancer Regression off-treatment and effective Reintroduction Therapy with an Anti-PD-1 Antibody," Clinical Cancer Research 19(42):462-468, American Association for Cancer Research, United States (2013).

Llosa, N.J., et al., "Immune checkpoints expression in MSI versus MSS colorectal cancers and their potential therapeutic implications," Journal of Clinical Oncology 32(15): 3620-3620, American Society of Clinical Oncology Journal, United States (2014).

Rahman, N., "Mainstreaming genetic testing of cancer predisposition genes," Clinical Medicine 14(4):436-439, Royal College of Physicians, United Kingdom (2014).

Gatalica, Z., et al., "High Microsatellite instability (MSI-H) colorectal carcinoma: a brief review of predictive biomarkers in the era of personalized medicine," Fam Cancer 15(3):405-412, Springerlink, United States (Feb. 2016).

Patel, S.P. et al., "Modulation of Immune System Inhibitory Checkpoints in Colorectal Cancer," Curr Colorectal Cancer Rep 9:391-397, Springerlink, United States (2013).

Anonymous: "A Study of Nivolumab and Nivolumab Plus Ipilimumab in Recurrent and Metastatic Colon Cancer (CheckMate 142)". Retrieved from the Internet: URL: https://clinicaltrials.gov/ct2/history/NCT02060188?V_49=View#StudyPageTop [retrieved on Aug. 6, 2021], 22 pages.

METHODS OF TREATING COLORECTAL CANCER

FIELD OF THE DISCLOSURE

This disclosure relates to methods for treating a tumor derived from a colorectal cancer exhibiting a high degree of microsatellite instability (MSI-H) in a subject in need thereof comprising administering to the subject an anti-Programmed Death-1 (PD-1) antibody. In some embodiments, the anti-PD-1 antibody is administered in combination with an anti-Cytotoxic T-Lymphocyte Antigen-4 (CTLA-4) antibody. In some embodiments, the colorectal cancer is rectal cancer, colon cancer, or any combination thereof.

BACKGROUND OF THE DISCLOSURE

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody (Ab), ipilimumab (YERVOY®), that binds to and inhibits CTLA-4 for the treatment of patients with advanced melanoma (Hodi et al. (2010) *N Engl J Med* 363:711-23) and the development of antibodies such as nivolumab and pembrolizumab (formerly lambrolizumab; USAN Council Statement, 2013) that bind specifically to the Programmed Death-1 (PD-1) receptor and block the inhibitory PD-1/PD-1 ligand pathway (Topalian et al. *N Engl J Med* 366:2443-54 (2012a); Topalian et al. *Curr Opin Immunol* 24:207-12 (2012b); Topalian et al. *J Clin Oncol* 32(10):1020-30 (2014); Hamid et al. *N Engl J Med* 369:134-144 (2013); Hamid and Carvajal *Expert Opin Biol Ther* 13(6):847-61 (2013); McDermott and Atkins *Cancer Med* 2(5):662-73(2013)).

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., (2014) *Cancer Immunol Res* 2:846-56). Nivolumab has shown activity in a variety of advanced solid tumors including renal cell carcinoma (renal adenocarcinoma, or hypernephroma), melanoma, and non-small cell lung cancer (NSCLC) (Topalian et al., (2012) N Engl J Med 366:2443-54; Topalian et al., (2014) J Clin Oncol 32:1020-30; Drake et al., (2013) BJU Int 112:1-17; Ansell et al., (2015) Blood 126:583 [Abstract]; PCT Publication No. WO 2013/173223).

Colorectal cancer is the third most common type of cancer in both men and women in the U.S. (See http://www.cancer.gov/types/colorectal, last visited Dec. 9, 2015). Most colorectal cancers are adenocarcinomas. Some colorectal cancers are associated with a high degree of microsatellite instability (MSI-H), which results from impaired DNA mismatch repair. In particular, patients with DNA mismatch repair-deficient/microsatellite instability-high (dMMR/MSI-H) metastatic colorectal cancer (mCRC) (~5% of patients) are less likely to benefit from conventional chemotherapy than patients with proficient MMR (pMMR) mCRC. dMMR-MSI-H CRC is associated with a high mutational burden and is particularly susceptible to immune checkpoint inhibitor blockade.

Targeted therapy of multiple non-redundant molecular pathways regulating immune responses may enhance antitumor immunotherapy. However, not all therapies are acceptable. There remains a need for therapies with an acceptable safety profile and high efficacy that enhance antitumor immune responses compared to monotherapy and other immunotherapy combinations.

SUMMARY OF THE DISCLOSURE

The present disclosure relates to a method for treating a subject afflicted with a tumor derived from a colorectal cancer exhibiting a high degree of microsatellite instability (MSI-H) comprising administering to the subject a therapeutically effective amount of an antibody or an antigen-binding portion thereof that binds specifically to Programmed Death-1 receptor (PD-1) and inhibits PD-1 activity ("anti-PD-1 antibody"). In some embodiments, the method further comprises administering a therapeutically effective amount of an antibody or antigen-binding portion thereof that specifically binds to Cytotoxic T-Lymphocyte Antigen-4 (CTLA-4) and inhibits CTLA-4 activity ("anti-CTLA-4 antibody").

In some embodiments, the colorectal cancer is rectal cancer, colon cancer, or any combination thereof. In one embodiment, the administering treats the colorectal cancer.

In some embodiments, the anti-PD-1 antibody cross-competes with nivolumab for binding to human PD-1. In some embodiments, the anti-PD-1 antibody binds to the same epitope as nivolumab. In certain embodiments, the anti-PD-1 antibody is a chimeric, humanized or human monoclonal antibody or a portion thereof. In some embodiments, the anti-PD-1 antibody comprises a heavy chain constant region which is of a human IgG1 or IgG4 isotype. In one embodiment, the anti-PD-1 antibody is nivolumab. In another embodiment, the anti-PD-1 antibody is pembrolizumab.

In certain embodiments, the anti-PD-1 antibody is administered at a dose ranging from at least about 0.1 mg/kg to at least about 10.0 mg/kg body weight once about every 1, 2 or 3 weeks. In one embodiment, the anti-PD-1 antibody (e.g., nivolumab) is administered at a dose of at least about 1 mg/kg body weight once about every 3 weeks. In another embodiment, the anti-PD-1 antibody (e.g., nivolumab) is administered at a dose of at least about 3 mg/kg body weight once about every 3 weeks. In yet another embodiment, the anti-PD-1 antibody (e.g., nivolumab) is administered at a dose of at least about 3 mg/kg body weight once about every 2 weeks. In other embodiments, the anti-PD-1 antibody (e.g., pembrolizumab) is administered at a dose of at least about 200 mg every 3 weeks or 2 mg/kg (up to 200 mg) every three weeks. In some embodiments, the anti-PD-1 antibody (e.g., avelumab) is administered at a dose of 10 mg/kg every two weeks. In certain embodiments, the anti-PD-1 antibody is administered at a flat dose. In embodiments, the anti-PD-1 antibody is administered at a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 550 mg, at least about 600 mg, at least about 650 mg, at least 700 mg, at least 750 mg, or at least 800 mg. In some embodiments, the anti-PD-1 antibody is administered for as long as clinical benefit is observed or until unmanageable toxicity or disease progression occurs.

In some embodiments, the anti-CTLA-4 antibody cross-competes with ipilimumab for binding to human CTLA-4. In one embodiment, the anti-CTLA-4 antibody binds to the same epitope as ipilimumab. In some embodiments, the anti-CTLA-4 antibody is a chimeric, humanized or human monoclonal antibody or a portion thereof. In certain embodiments, the anti-CTLA-4 antibody comprises a heavy chain constant region which is of a human IgG1 or IgG2 isotype. In one embodiment, the anti-CTLA-4 antibody is ipilimumab. In another embodiment, the anti-CTLA-4 antibody is tremelimumab.

In some embodiments, the anti-CTLA-4 antibody is administered at a dose ranging from at least about 0.01 mg/kg to at least about 10 mg/kg body weight once about every 1, 2 or 3 weeks. In one embodiment, the anti-CTLA-4 antibody is administered at a dose of at least about 1 mg/kg body weight once about every 3 weeks. In another embodiment, the anti-CTLA-4 antibody is administered at a dose of at least about 3 mg/kg body weight once about every 3 weeks. In some embodiments, the anti-CTLA-4 antibody is administered for as long as clinical benefit is observed or until unmanageable toxicity or disease progression occurs.

In some embodiments, the anti-PD-1 and anti-CTLA-4 antibodies are formulated for intravenous administration. In certain embodiments, the anti-PD-1 and anti-CTLA-4 antibodies are administered sequentially. In one embodiment, the anti-PD-1 and anti-CTLA-4 antibodies are administered within 30 minutes of each other. In an embodiment, the anti-PD-1 antibody is administered before the anti-CTLA-4 antibody. In another embodiment, the anti-CTLA-4 antibody is administered before the anti-PD-1 antibody. In certain embodiments, the anti-PD-1 antibody and the anti-CTLA-4 antibody are administered concurrently in separate compositions. In other embodiments, the anti-PD-1 antibody and the anti-CTLA-4 antibody are admixed as a single composition for concurrent administration.

In one embodiment, the anti-PD-1 antibody is administered at a subtherapeutic dose. In another embodiment, the anti-CTLA-4 antibody is administered at a subtherapeutic dose. In a further embodiment, the anti-PD-1 antibody and the anti-CTLA-4 antibody are each administered at a subtherapeutic dose.

In certain embodiments, the subject has a tumor that expresses PD-L1, PD-L2, or both. In embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

The present disclosure relates to a kit for treating a subject afflicted with a cancer, the kit comprising: (a) a dosage ranging from about 0.1 mg/kg to about 10 mg/kg of an anti-PD-1 antibody; (b) a dosage ranging from about 0.1 mg/kg to about 10 mg/kg of an anti-CTLA-4 antibody; and (c) instructions for using the anti-PD-1 antibody and the anti-CTLA-4 antibody in any method disclosed herein.

In some embodiments, the subject has a microsatellite stable (MSS) tumor or a microsatellite instability-high (MSI-H) tumor. Certain embodiments further comprise measuring the microsatellite status of a tumor prior to administration of an anti-PD-1 antibody and/or an anti-CTLA-4 antibody. In embodiments, the tumor is a MSS tumor or a MSI-H tumor. In one embodiment, the subject is afflicted with a colorectal cancer. In another embodiment, the subject is afflicted with colon cancer. In yet another embodiment, the subject is afflicted with a rectal cancer.

EMBODIMENTS

E1. A method for treating a subject afflicted with a tumor derived from a colorectal cancer comprising administering to the subject a therapeutically effective amount of an antibody or an antigen-binding portion thereof that binds specifically to Programmed Death-1 receptor (PD-1) and inhibits PD-1 activity ("anti-PD-1 antibody"), wherein the tumor exhibits a high degree of microsatellite instability ("MSI-H").

E2. The method of embodiment E1, wherein the tumor is a colon cancer.

E3. The method of embodiment E1, wherein the tumor is a rectal cancer.

E4. The method of any one of embodiments E1 to E3, wherein the tumor exhibits one or more characteristics selected from the group consisting of: (a) the tumor comprises a germline alteration in at least two, at least three, at least four, or at least five DNA mismatch repair genes ("MMR genes"); (b) the tumor comprises a germline alteration in at least 30% of five or more MMR genes; (c) at least one protein encoded by DNA MMR genes is not detected in the tumor; and (d) any combination thereof.

E5. The method of embodiment E4, wherein the DNA MMR genes comprise MSH2, MLH1, MSH6, PMS2, PMS1, or any combination thereof.

E6. The method of embodiment E4, wherein the germline alternation in (a) or (b) is measured by a polymerase chain reaction.

E7. The method of embodiment E4, wherein the at least one protein encoded by DNA MMR genes is detected by an immunohistochemistry.

E8. The method of any one of embodiments E1 to E7, wherein the subject exhibits a progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months after the administration of treatment.

E9. The method of any one of embodiments E1 to E8, wherein the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months after the administration of treatment.

E10. The method of any one of embodiments E1 to E9, wherein the administering treats the cancer.

E11. The method of any one of embodiments E1 to E10, wherein the anti-PD-1 antibody cross-competes with nivolumab for binding to human PD-1.

E12. The method of any one of embodiments E1 to E11, wherein the anti-PD-1 antibody binds to the same epitope as nivolumab.

E13. The method of any one of embodiments E1 to E12, wherein the anti-PD-1 antibody is a chimeric, humanized or human monoclonal antibody or a portion thereof.

E14. The method of any one of embodiments E1 to E13, wherein the anti-PD-1 antibody comprises a heavy chain constant region which is of a human IgG1 or IgG4 isotype.

E15. The method of any one of embodiments E1 to E14, wherein the anti-PD-1 antibody is nivolumab.

E16. The method of any one of embodiments E1 to E14, wherein the anti-PD-1 antibody is pembrolizumab.

E17. The method of any one of embodiments E1 to E16, wherein the anti-PD-1 antibody is administered at a dose ranging from at least about 0.1 mg/kg to at least about 10.0 mg/kg body weight once about every 1, 2 or 3 weeks.

E18. The method of embodiment E17, wherein the anti-PD-1 antibody is administered at a dose of about 3 mg/kg body weight once about every 3 weeks.

E19. The method of any one of embodiments E1 to E18, further comprising administering a therapeutically effective amount of an antibody or antigen-binding portion thereof that specifically binds to CTLA-4 and inhibits CTLA-4 activity ("anti-CTLA-4 antibody").

E20. The method of embodiment E19, wherein the anti-CTLA-4 antibody cross-competes with ipilimumab for binding to human CTLA-4.

E21. The method of embodiment E19 or E20, wherein the anti-CTLA-4 antibody binds to the same epitope as ipilimumab.

E22. The method of any one of embodiments E19 to E21, wherein the anti-CTLA-4 antibody is a chimeric, humanized or human monoclonal antibody or a portion thereof.

E23. The method of any one of embodiments E19 to E22, wherein the anti-CTLA-4 antibody comprises a heavy chain constant region which is of a human IgG1 or IgG2 isotype.

E24. The method of any one of embodiments E19 to E23, wherein the anti-CTLA-4 antibody is ipilimumab.

E25. The method of any one of embodiments E19 to E23, wherein the anti-CTLA-4 antibody is tremelimumab.

E26. The method of any one of embodiments E19 to E25, wherein the anti-CTLA-4 antibody is administered at a dose ranging from at least about 0.1 mg/kg to at least about 10.0 mg/kg body weight once about every 1, 2 or 3 weeks.

E27. The method of embodiment E26, wherein the anti-CTLA-4 antibody is administered at a dose of about 1 mg/kg body weight once about every 3 weeks.

E28. The method of any one of embodiments E19 to E25, wherein the anti-PD-1 antibody is administered at a dose of about 1 mg/kg body weight and the anti-CTLA-4 antibody is administered at a dose of about 1 mg/kg body weight.

E29. The method of any one of embodiments E19 to E25, wherein the anti-PD-1 antibody is administered at a dose of about 1 mg/kg body weight and the anti-CTLA-4 antibody is administered at a dose of about 3 mg/kg body weight.

E30. The method of any one of embodiments E19 to E25, wherein the anti-PD-1 antibody is administered at a dose of about 3 mg/kg body weight and the anti-CTLA-4 antibody is administered at a dose of about 1 mg/kg body weight.

E31. The method of any one of embodiments E19 to E25, wherein the anti-PD-1 antibody is administered at a dose of about 3 mg/kg body weight and the anti-CTLA-4 antibody is administered at a dose of about 3 mg/kg body weight.

E32. The method of any one of embodiments E19 to E31, wherein the administration of an anti-PD-1 antibody and anti-CTLA-4 antibody is followed by an anti-PD-1 antibody monotherapy.

E33. The method of embodiment E32, wherein the anti-PD-1 antibody monotherapy comprises administering an anti-PD-1 antibody at a dose of about 1 mg/kg body weight.

E34. The method of embodiment E32, wherein the anti-PD-1 antibody monotherapy comprises administering an anti-PD-1 antibody at a dose of about 3 mg/kg body weight.

E35. The method of embodiment E32, wherein the anti-PD-1 antibody monotherapy comprises administering an anti-PD-1 antibody at a dose of about 4 mg/kg body weight.

E36. The method of any one of embodiments E19 to E35, wherein the anti-PD-1 antibody and anti-CTLA-4 antibody are administered once about every 1, 2, 3, or 4 weeks.

E37. The method of any one of embodiments E32 to E35, wherein the anti-PD-1 antibody monotherapy is administered once about every 1, 2, 3, or 4 weeks.

E38. The method of any one of embodiments E1 to E37, wherein the subject exhibits a complete response or partial response to treatment at about 4 weeks, about 5 weeks, about 6 weeks, about 7 weeks, about 8 weeks, about 9 weeks, about 10 weeks, about 11 weeks, about 12 weeks, about 18 weeks, about 24 weeks, about 30 weeks, or about 36 weeks following the initial administration of treatment.

E39. The method of any one of embodiments E19 to E38, wherein the anti-PD-1 and anti-CTLA-4 antibodies are formulated for intravenous administration.

E40. The method of any one of embodiments E19 to E39, wherein the anti-PD-1 and anti-CTLA-4 antibodies are administered sequentially.

E41. The method of any one of embodiments E19 to E40, wherein the anti-PD-1 and anti-CTLA-4 antibodies are administered within 30 minutes of each other.

E42. The method of any one of embodiments E19 to E41, wherein the anti-PD-1 antibody is administered before the anti-CTLA-4 antibody.

E43. The method of any one of embodiments E19 to E41, wherein the anti-CTLA-4 antibody is administered before the anti-PD-1 antibody.

E44. The method of any one of embodiments E1 to E39, wherein the anti-PD-1 antibody and the anti-CTLA-4 antibody are administered concurrently in separate compositions.

E45. The method of any one of embodiments E1 to E39, wherein the anti-PD-1 antibody and the anti-CTLA-4 antibody are admixed as a single composition for concurrent administration.

E46. A kit for treating a patient afflicted with a tumor derived from colorectal cancer, wherein the tumor exhibits a high degree of microsatellite instability ("MSI-H"), the kit comprising: (a) a dosage ranging from 0.1 mg/kg to 10 mg/kg body weight of an anti-PD-1 antibody; (b) a dosage ranging from 0.1 mg/kg to 10 mg/kg body weight of an anti-CTLA-4 antibody; and (c) instructions for using the anti-PD-1 antibody and the anti-CTLA-4 antibody in the method of any one of embodiments E1 to E45.

DETAILED DESCRIPTION OF THE DISCLOSURE

Figure 1:
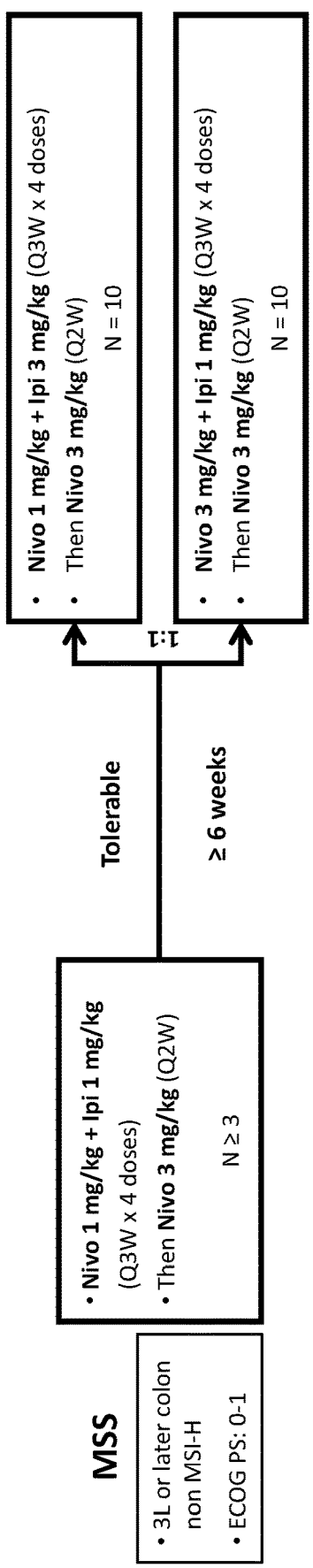
FIG. 1 shows a study schematic for microsatellite stable (MSS) colorectal cancer patients receiving 1 mg/kg of nivolumab in combination with 3 mg/kg of ipilimumab or 3 mg/kg of nivolumamb in combination with 1 mg/kg ipilimumab.

This disclosure relates to methods for treating a colorectal cancer in a subject comprising administering to the subject an anti-Programmed Death-1 (PD-1) antibody. In some embodiments, the colorectal cancer exhibits a high degree of microsatellite instability (MSI-H). In some embodiments, the method further comprises administering an anti-Cytotoxic T-Lymphocyte Antigen-4 (CTLA-4) antibody. In some embodiments, the colorectal cancer is rectal cancer, colon cancer, or any combination thereof.

Terms

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a therapeutic agent to a subject, using any of the various methods and delivery systems known to those skilled in the art. Exemplary routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent may be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody may be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies may be produced by hybridoma, recombinant, transgenic or other techniques known to those skilled in the art.

A "human" antibody (HuMAb) refers to an antibody having variable regions in which both the framework and CDRs are derived from human germline immunoglobulin sequences. Furthermore, if the antibody contains a constant region, the constant region also is derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDRs of a non-human antibody are replaced with corresponding amino acids derived from human immunoglobulins. In one embodiment of a humanized form of an antibody, some, most or all of the amino acids outside the CDRs have been replaced with amino acids from human immunoglobulins, whereas some, most or all amino acids within one or more CDRs are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody. In some embodiments, the CDRs of a humanized antibody contain CDRs from a non-human, mammalian antibody. In other embodiments, the CDRs of a humanized antibody contain CDRs from an engineered, synthetic antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and may also metastasize to distant parts of the body through the lymphatic system or bloodstream. Following metastasis, the distal tumors can be said to be "derived from" the original, pre-metastasis tumor. For example, a "tumor derived from" a colorectal cancer refers to a tumor that is the result of a metastasized colorectal cancer. Because the distal tumor is derived from the pre-metastasis tumor, the "derived from" tumor can also comprise the pre-metastasis tumor, e.g., a tumor derived from a colorectal cancer can comprise a colorectal cancer.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" or "PD-L2 positive" as used herein can be interchangeably used with "PD-L1 and/or PD-L2 expression of at least about 1%." In one embodiment, the PD-L1 and/or PD-L2 expression can be used by any methods known in the art. In another embodiment, the PD-L1 and/or PD-L2 expression is measured by an automated in situ hybridization (IHC). A PD-L1 and/or PD-L2 positive tumor can thus have at least about 1%, at least about 2%, at least about 5%, at least about 10%, or at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of tumor cells expressing PD-L1 and/or PD-L2 as measured by an automated IHC. In certain embodiments, "PD-L1 positive" means that there are at least 100 cells that express PD-L1 on the surface of the cells. In other embodiments, "PD-L2 positive" means that there are at least 100 cells that express PD-L2 on the surface of the cells.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that down regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or non-human animal. The term "non-human animal" includes, but is not limited to, vertebrates such as non-human primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, by at least about 80%, by at least about 90%, or about 100% relative to untreated subjects.

In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight-based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the disclosure means that two or more different antibodies in a single composition (e.g., anti-PD-1 antibody and anti-CTLA-4 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CTLA-4 antibody). For example, the 3:1 ratio of an anti-PD-1 antibody and an anti-CTLA-4 antibody can mean that a vial can contain about 240 mg of the anti-PD-1 antibody and 80 mg of the anti-CTLA-4 antibody or about 3 mg/ml of the anti-PD-1 antibody and 1 mg/ml of the anti-CTLA-4 antibody.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-CTLA-4 antibody and/or anti-PD-1 antibody). For example, a 60 kg person and a 100 kg person would receive the same dose of an antibody (e.g., 240 mg of an anti-PD1 antibody).

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

TABLE 1

List of Abbreviations

| Term | Definition |
| --- | --- |
| AEs | adverse events |
| BMS | Bristol-Myers Squibb |
| CRC | colorectal cancer |
| CI | confidence interval |
| CR | complete remission |
| DOR | duration of response |
| Kg | kilogram |
| mAB | monoclonal antibody |
| Mg | milligram |
| N | number of subjects or observations |
| NE | not evaluable |
| ORR | overall response rate |
| OS | overall survival |
| PD | progressive disease |
| PD-1 | programmed death-1 |
| PD-L1 | programmed death-ligand 1 |
| PD-L2 | programmed death-ligand 2 |
| PFS | progression-free survival |
| PR | partial remission |
| SAE | serious adverse event |
| SD | stable disease |
| SOP | Standard Operating Procedures |
| Subj | subject |

Methods of the Disclosure

The present disclosure is directed to a method for treating a subject afflicted with a tumor derived from a colorectal cancer comprising administering to the subject a therapeutically effective amount of an antibody or an antigen-binding portion thereof that binds specifically to a Programmed Death-1 receptor (PD-1) and inhibits PD-1 activity ("anti-PD-1 antibody") or an antibody or an antigen-binding portion thereof that binds specifically to a Programmed Death-Ligand 1 (PD-L1) and inhibits PD-L1 activity ("anti-PD-L1 antibody").

In some embodiments, the therapy treats a tumor derived from a cancer, which is colorectal cancer. In some embodiments, the colorectal cancer is colon cancer. In other embodiments, the colorectal cancer is rectal cancer. In certain embodiments, the colorectal cancer has microsatellite instability (MSI) (See Pawlik et al., *Dis. Markers* 20(4-5): 199-206 (2004)). In other embodiments, the colorectal cancer has high microsatellite instability (MSI-H).

Colon cancer presents in five stages: Stage 0 (Carcinoma in Situ), Stage I, Stage II, Stage III and Stage IV. Six types of standard treatment are used for colon cancer: 1) surgery, including a local excision, resection of the colon with anastomosis, or resection of the colon with colostomy; 2) radiofrequency ablation; 3) cryosurgery; 4) chemotherapy; 5) radiation therapy; and 6) targeted therapies, including monoclonal antibodies and angiogenesis inhibitors. In some embodiments, the combination therapy of the disclosure treats a colon cancer along with a standard of care therapy.

Rectal cancer presents in five stages: Stage 0 (Carcinoma in Situ), Stage I, Stage II, Stage III and Stage IV. Six types of standard treatment are used for rectal cancer: 1) Surgery, including polypectomy, local excision, resection, radiofrequency ablation, cryosurgery, and pelvic exenteration; 2) radiation therapy; 3) chemotherapy; and 4) targeted therapy, including monoclonal antibody therapy. In some embodiments, the methods of the disclosure treats a rectal cancer along with a standard of care therapy.

In colorectal cancer, MSI-H is associated with increases in immune infiltration and expression of immune checkpoint regulators. Therefore, the methods of the disclosure include treatment of a colorectal cancer exhibiting a high degree of microsatellite instability (MSI-H). In some embodiments, the anti-PD-1 antibody is administered in combination with a therapeutically effective amount of an antibody or an antigen-binding portion thereof that binds specifically to CTLA-4 ("anti-CTLA-4 antibody").

Microsatellite instability is the condition of genetic hypermutability that results from impaired DNA mismatch repair (MMR). The presence of MSI represents phenotypic evidence that MMR is not functioning normally. In most cases, the genetic basis for instability in MSI tumors is an inherited germline alteration in any one of the five human MMR genes: MSH2, MLH1, MSH6, PMS2, and PMS1. In certain embodiments, the subject receiving tumor treatment has a high degree of microsatellite instability (MSI-H) and has at least one mutation in genes MSH2, MLH1, MSH6, PMS2, or PMS1. In other embodiments, subjects receiving tumor treatment within a control group have no microsatellite instability (MSS or MSI stable) and has no mutation in genes MSH2, MLH1, MSH6, PMS2, and PMS1.

The present disclosure is also directed to methods of treating a tumor, e.g., tumor in colon, comprising identifying a subject responsive to an anti-PD-1 antibody administered alone or in combination with an anti-CTLA-4 antibody, wherein the subject has a MSI-H tumor. In some embodiments, the disclosure provides a method of treating a tumor, e.g., a tumor in colon, comprising (i) identifying a subject who has a tumor that is a MSI-H tumor and (ii) administering an effective amount of an anti-PD-1 antibody alone or in combination with an effective amount of an anti-CTLA-4 antibody to the subject. As used herein, MSI-H tumors mean tumors having greater than at least about 30% of unstable MSI biomarkers. In some embodiments, a colorectal cancer is MSI-H when a germline alteration is detected in at least two, at least three, at least four, or at least five MMR genes. In other embodiments, a colorectal cancer is MSI-H when a germline alteration is detected in at least 30% of five or more MMR genes. In some embodiments, a germline alternation in MMR genes is measured by a polymerase chain reaction. In other embodiments, a colorectal cancer is MSI-H when at least one protein encoded by DNA MMR genes is not detected in the tumor. In some embodiments, the at least one protein encoded by DNA MMR genes is detected by an immunohistochemistry. In certain embodiments, the present disclosure is directed to a method of treating a cancer comprising 1) identifying the microsatellite status of a tumor and 2) administering a therapy to the subject based on the microsatellite status. In some embodiments, the subject has MSI-H.

In some embodiments, the colorectal cancer is rectal cancer, colon cancer, or any combination thereof. In certain embodiments, the subject has received one, two, three, four, five or more prior cancer treatments. In other embodiments, the subject is treatment-naïve. In some embodiments, the subject has progressed on other cancer treatments. In embodiments, the cancer has reoccurred. In some embodiments, the cancer is metastatic. In other embodiments, the cancer is not metastatic.

In some embodiments, the colorectal cancer is histologically confirmed. In certain embodiments, the colorectal cancer is metastatic or recurrent. In embodiments, the subject has had progression during, after, or been intolerant following the last administration of standard therapies. In certain embodiments, the subject has microsatellite instability. In other embodiments, the colorectal cancer has a high degree of microsatellite instability (MSI-H).

In other embodiments, the colorectal cancer that has MSI-H expresses PD-L1. In yet other embodiments, the colorectal cancer that has MSI-H expresses at least 1%, at least 2%, at least 3%, at least 4%, at least 5%, at least 10%, at least 20%, at least 30%, at least 40%, or at least 50% membrane PD-L1.

In some embodiments, the present methods comprise administering an effective amount of an anti-PD-1 antibody. In other embodiments, the present methods comprise administering an effective amount of an anti-PD-1 antibody and an effective amount of an anti-CTLA-4 antibody. An effective amount of an anti-PD-1 antibody and/or an anti-CTLA-4 antibody can be a flat dose or a weight based dose.

In embodiments, the disclosure includes a method of treating a subject afflicted with a tumor derived from colorectal cancer comprising administering an anti-PD-1 antagonist in combination with an anti-CTLA-4 antibody to treat cancer. An "anti-PD-1 antagonist" as referred herein includes any molecule that inhibits interaction between PD-1 (receptor) and PD-L1 (ligand) such that the signal pathway of PD-1/PD-L1 is blocked. In other embodiments, an anti-PD-1 antagonist is a PD-1-Fc fusion protein. In certain embodiments, an anti-PD-1 antagonist includes an anti-PD-1 fusion protein, an antisense molecule, a small molecule, a ribozyme, or a nanobody that inhibits or prevents interaction between PD-1 and PD-L1.

In certain embodiments, the therapy of the present disclosure (e.g., administration of an anti-PD-1 antibody alone or in combination with an anti-CTLA-4 antibody) effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year or more.

In certain embodiments, the therapy of the present disclosure effectively increases the duration of progression-free survival of the subject. For example, the progression free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year. In certain embodiments, the therapy of the present disclosure effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99% or about 100%.

In some embodiments, the anti-PD-1 antibody is formulated for intravenous administration. In some embodiments, the anti-PD-1 and anti-CTLA-4 antibodies are formulated for intravenous administration. In certain embodiments, the anti-PD-1 and anti-CTLA-4 antibodies are administered sequentially. In embodiments, the anti-PD-1 and anti-CTLA-4 antibodies are administered within 30 minutes of each other. In one embodiment, the anti-PD-1 antibody or antigen-binding portion thereof is administered before the anti-CTLA-4 antibody or antigen-binding portion thereof. In another embodiment, the anti-CTLA-4 antibody or antigen-binding portion thereof is administered before the anti-PD-1 antibody or antigen-binding portion thereof. In another embodiment, the anti-PD-1 antibody or antigen-binding portion thereof and the anti-CTLA-4 antibody or antigen-binding portion thereof are administered concurrently in separate compositions. In a further embodiment, the anti-PD-1 antibody or antigen-binding portion thereof and the anti-CTLA-4 antibody or antigen-binding portion thereof are admixed as a single composition for concurrent administration.

In some embodiments, the anti-PD-1 antibody and anti-CTLA-4 antibody are administered in a fixed dose.

In some embodiments, the cancer is microsatellite stable (MSS) (or "MSI stable") and therefore has no microsatellite instability. In other embodiments, the cancer has a high degree of microsatellite instability (MSI-H).

Anti-PD-1 Antibodies and Anti-PD-L1 Antibodies

The therapy of the present disclosure can utilize an anti-PD-1 antibody or an antigen-binding portion thereof. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Anti-PD-1 antibodies suitable for use in the disclosed methods are antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 "antibody" includes an antigen-binding portion that binds to the PD-1 or PD-L1 receptor, respectively, and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-L1 antibody or antigen-binding fragment thereof competes for binding with BMS-936559, MPDL3280A, MEDI4736, or MSB0010718C for binding to human PD-L1.

In other embodiments, the anti-PD-1 antibody or anti-PD-L1 antibody, or antigen-binding portions thereof is a chimeric, humanized, or human monoclonal antibody or a portion thereof. In certain embodiments for treating a human subject, the antibody is a humanized antibody. In other embodiments for treating a human subject, the antibody is a human antibody of an IgG1, IgG2, IgG3, or IgG4 isotype can be used.

In certain embodiments, the anti-PD-1 antibody, or anti-PD-L1 antibody, or antigen-binding portions thereof comprises a heavy chain constant region which is of a human IgG1 or IgG4 isotype. In certain other embodiments, the sequence of the IgG4 heavy chain constant region of the anti-PD-1 antibody or anti-PD-L1 antibody, or antigen-binding portions thereof, contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., In vitro characterization of the anti-PD-1 antibody nivolumab, BMS-936558, and in vivo toxicology in non-human primates, *Cancer Imm Res,* 2(9):846-56 (2014)). In yet other embodiments, the antibody comprises a light chain constant region which is a human kappa or lambda constant region. In other embodiments, the anti-PD-1 antibody, or anti-PD-L1 antibody, or antigen-binding portions thereof is a monoclonal antibody or an antigen-binding portion thereof.

Human monoclonal antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and/or (j) inhibits tumor cell growth in vivo. Anti-PD-1 antibodies usable in the present disclosure include monoclonal antibodies that bind specifically to human PD-1 and exhibit at least one, at least two, at least three, at least four or at least five of the preceding characteristics. In some embodiments, the anti-PD-1 antibody comprises nivolumab. In one embodiment, the anti-PD-1 antibody comprises pembrolizumab.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9): 846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223). In another embodiment, the anti-PD-1 antibody (or antigen-binding portion thereof) cross-competes with nivolumab. In some embodiments, the anti-PD-1 antibody binds to the same epitope as nivolumab. In certain embodiments, the anti-PD-1 antibody has the same CDRs as nivolumab.

In another embodiment, the anti-PD-1 antibody (or antigen-binding portion thereof) cross-competes with pembrolizumab. In some embodiments, the anti-PD-1 antibody binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also www.cancer.gov/drugdictionary?cdrid=695789 (last accessed: Dec. 14, 2014). Pembrolizumab has been approved by the FDA for the treatment of relapsed or refractory melanoma and advanced NSCLC.

In other embodiments, the anti-PD-1 antibody (or antigen-binding portion thereof) cross-competes with MEDI0680. In some embodiments, the anti-PD-1 antibody binds to the same epitope as MEDI0680. In certain embodiments, the anti-PD-1 antibody has the same CDRs as MEDI0680. In other embodiments, the anti-PD-1 antibody is MEDI0680 (formerly AMP-514), which is a monoclonal antibody against the PD-1 receptor. MEDI0680 is described, for example, in U.S. Pat. No. 8,609,089 B2 or in www.cancer.gov/drugdictionary?cdrid=756047 (last accessed Dec. 14, 2014).

In certain embodiments, an immune checkpoint inhibitor is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody (or antigen-binding portion thereof) cross-competes with BGB-A317. In some embodiments, the anti-PD-1 antibody binds to the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In other embodiments, the anti-PD-1 antibody (or antigen-binding portion thereof) cross-competes with INCSHR1210 (SHR-1210). In some embodiments, the anti-PD-1 antibody binds to the same epitope as INCSHR1210 (SHR-1210). In certain embodiments, the anti-PD-1 antibody has the same CDRs as INCSHR1210 (SHR-1210). In certain embodiments, the anti-PD-1 antibody is INCSHR1210 (SHR-1210), which is a human monoclonal antibody. INCSHR1210 (SHR-1210) is described in WO2015/085847.

In other embodiments, the anti-PD-1 antibody (or antigen-binding portion thereof) cross-competes with REGN-2810. In some embodiments, the anti-PD-1 antibody binds to the same epitope as REGN-2810. In certain embodiments, the anti-PD-1 antibody has the same CDRs as REGN-2810. In certain embodiments, the anti-PD-1 antibody is REGN-2810, which is a human monoclonal antibody. REGN-2810 is described in WO2015/112800.

In other embodiments, the anti-PD-1 antibody (or antigen-binding portion thereof) cross-competes with PDR001. In some embodiments, the anti-PD-1 antibody binds to the same epitope as PDR001. In certain embodiments, the anti-PD-1 antibody has the same CDRs as PDR001. In certain embodiments, the anti-PD-1 antibody is PDR001, which is a humanized monoclonal antibody. PDR001 is described in WO2015/112900.

In other embodiments, the anti-PD-1 antibody (or antigen-binding portion thereof) cross-competes with TSR-042 (ANB011). In some embodiments, the anti-PD-1 antibody binds to the same epitope as TSR-042 (ANB011). In certain embodiments, the anti-PD-1 antibody has the same CDRs as TSR-042 (ANB011). In certain embodiments, the anti-PD-1 antibody is TSR-042 (ANB011), which is a humanized monoclonal antibody. TSR-042 (ANB011) is described in WO2014/179664.

In other embodiments, the anti-PD-1 antibody (or antigen-binding portion thereof) cross-competes with STI-1110. In some embodiments, the anti-PD-1 antibody binds to the same epitope as STI-1110. In certain embodiments, the anti-PD-1 antibody has the same CDRs as STI-1110. In certain embodiments, the anti-PD-1 antibody is STI-1110, which is a human monoclonal antibody. STI-1110 is described in WO2014/194302.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as nivolumab are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art.

Anti-PD-1 antibodies usable in the methods of this disclosure also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; or any combination thereof.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0680 (formerly AMP-514), AMP-224, or BGB-A317.

In other embodiments, the anti-PD-1 antibody or antigen-binding portion thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3 or IgG4 isotype may be used.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present disclosure is directed to a method for treating a subject afflicted with a tumor derived from a colorectal cancer comprising administering to the subject a therapeutically effective amount of an anti-cancer agent which is an antibody or an antigen-binding portion thereof that binds specifically to a Programmed Death-Ligand 1 (PD-L1) receptor and inhibits PD-L1 activity (an anti-PD-L1 antibody). In other embodiments, the present disclosure is directed to a method for treating a subject afflicted with a tumor derived from a colorectal cancer comprising administering to the subject a therapeutically effective amount of an anti-PD-L1 antibody in combination with an anti-CTLA-4 antibody. In certain embodiments, the anti-PD-L1 Ab is BMS-936559 (formerly 12A4 or MDX-1105) (see, e.g., U.S. Pat. No. 7,943,743; WO 2013/173223). In other embodiments, the anti-PD-L1 Ab is MPDL3280A (also known as RG7446 or atezolizumab) (see, e.g., Herbst; U.S. Pat. No. 8,217,149), MEDI4736 (also called Durvalumab; Khleif, 2013, See U.S. Pat. No. 8,779,108 or US 2014/0356353, filed May 6, 2014), or MSB0010718C (also called Avelumab; See US 2014/0341917). In other embodiments, the anti-PD-L1 antibody is CX-072 (also called CytomX; See WO2016/149201)

Anti-CTLA-4 Antibodies

In some embodiments, the methods of the present disclosure can be a combination therapy of an anti-PD-1 antibody or an anti-PD-L1 antibody and an anti-CTLA-4 antibody. Anti-CTLA-4 antibodies of the instant disclosure bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. Nos. 6,984,720 and 7,605,238. Other anti-PD-1 monoclonal antibodies have been described in, for example, U.S. Pat. Nos. 5,977,318, 6,051,227, 6,682,736, and 7,034,121. The anti-PD-1 human monoclonal antibodies disclosed in U.S. Pat. No. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present disclosure include monoclonal antibodies that bind specifically to human CTLA-4 and exhibit at least one, at least two, or at least three of the preceding characteristics.

An exemplary clinical anti-CTLA-4 antibody is the human monoclonal antibody 10D1 (now known as ipilimumab and marketed as) YERVOY® as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies useful for the disclosed composition also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are chimeric antibodies, or humanized or human antibodies. Useful anti-CTLA-4 antibodies also include antigen-binding portions of the above antibodies such as Fab, F(ab')$_2$, Fd, or Fv fragments.

Cancer and Standard-of-Care Therapies

In some embodiments, the methods disclosed herein are used in place of standard of care therapies. In certain embodiments, a standard of care therapy is used in combination with any method disclosed herein. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2014).

Pharmaceutical Compositions and Dosages

Therapeutic agents of the present disclosure can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In some embodiments, the carrier for a composition containing an antibody is suitable for intravenous, intramuscular, subcutaneous, parenteral, spinal or epidermal administration (e.g., by injection or infusion). A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. In some embodiments, the anti-PD-1 antibody is administered at a weight-based dose. For administration of an anti-PD-1 antibody, the dosage can range from at least about 0.01 to at least about 20 mg/kg, from at least about 0.1 to at least about 10 mg/kg, of the subject's body weight. For example, dosages can be at least about 0.1 mg/kg, at least about 0.3 mg/kg, at least about 1 mg/kg, at least about 2 mg/kg, at least about 3 mg/kg, at least about 5 mg/kg, or at least about 10 mg/kg body weight. In certain embodiments, the dosage of the anti-PD-1 antibody is 3 mg/kg body weight. In certain embodiments, an anti-PD-1 antibody is administered at a flat dose. In certain embodiments, the flat dose of the anti-PD-1 antibody is a dose (e.g., flat dose) of at least about 100-300 mg, such as, at least about 200-300 mg, at least about 220-260 mg, at least about 230-250 mg or at least about 240 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg or at least about 300 mg. In some embodiments, the anti-PD-1 antibody is administered in a fixed dose with the anti-CTLA-4 antibody. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg anti-PD-1 antibody to mg anti-CTLA-4 antibody.

The dosing schedule is typically designed to achieve exposures that result in sustained receptor occupancy (RO) based on typical pharmacokinetic properties of an antibody. An exemplary treatment regime entails administration once per week, once about every 2 weeks, once about every 3 weeks, once about every 4 weeks, once about a month, about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment.

When used in combinations with other anti-cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity.

In some embodiments, the anti-CTLA-4 antibody is administered at a weight-based dose. For administration of an anti-CTLA-4 antibody the dosage can range from about 0.01 to about 20 mg/kg, about 0.05 to about 20 mg/kg, about 0.1 to about 20 mg/kg, about 0.1 to about 15 mg/kg, about 0.1 to about 10 mg/kg, about 0.1 to about 5 mg/kg, and about 1 to about 10 mg/kg of the subject's body weight. For example, dosages can be about 0.05 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 20 mg/kg of the subject's body weight. In some embodiments, the dosage of the anti-CTLA-4 antibody is 0.1 mg/kg body weight. In other embodiments, the dosage of the anti-CTLA-4 antibody is 1 mg/kg body weight. In further embodiments, the dosage of the anti-CTLA-4 antibody is 10 mg/kg body weight. In certain embodiments, an anti-CTLA-4 antibody is administered at a flat dose. In embodiments, the flat dose of the anti-CTLA-4 is a dose (e.g., flat dose) of at least about 60-1500 mg, such as, at least about 100-1400 mg, at least about 100-1000 mg, at least about 200-1000 mg or at least about 200-500 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, or at least about 1500 mg.

An exemplary treatment regime entails administration once per week, once about every 2 weeks, once about every 3 weeks, once about every 4 weeks, once about a month, once about every 3-6 months or longer. In certain embodiments, the anti-CTLA-4 antibody is administered once about every 3 weeks.

In some embodiments, a subtherapeutic dose of an anti-CTLA-4 antibody is used in the methods herein. The subtherapeutic dosages of an anti-CTLA-4 antibody used in the methods herein are higher than 0.001 mg/kg and lower than 10 mg/kg. In some embodiments, the subtherapeutic dose is about 0.001 mg/kg to about 10 mg/kg, about 0.01 mg/kg to about 10 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, at least about 1.0 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, or at least about 10 mg/kg body weight. In some embodiments, the subtherapeutic dose is about 10 mg/kg, about 5 mg/kg, about 2 mg/kg, about 1 mg/kg, about 0.1 mg/kg, or about 0.01 mg/kg body weight.

In certain embodiments, at least about 0.1 to about 10 mg/kg of the anti-CTLA-4 antibody and at least about 0.1 to about 10 mg/kg of the anti-PD1 antibody are administered to the subject once about every three weeks. In certain embodiments, at least about 1 mg/kg of the anti-CTLA-4 antibody and at least about 1 mg/kg of the anti-PD1 antibody are administered to the subject once about every three weeks. In certain embodiments, at least about 1 mg/kg of the anti-CTLA-4 antibody and at least about 3 mg/kg of the anti-PD1 antibody are administered to the subject once about every three weeks. In certain embodiments, at least about 3 mg/kg of the anti-CTLA-4 antibody and at least about 1 mg/kg of the anti-PD-1 antibody are administered to the subject one about every three weeks. In certain embodiments, at least about 3 mg/kg of the anti-CTLA-4 antibody and at least about 3 mg/kg of the anti-PD1 antibody are administered to the subject once about every three weeks. In embodiments, the anti-CTLA-4 antibody is ipilimumab. In some embodiments, the anti-PD-1 antibody is nivolumab.

In certain embodiments, the combination of an anti-PD-1 antibody and an anti-CTLA-4 antibody is administered intravenously to the subject once about every 3 weeks for a total of 12 weeks. In some embodiments, the 12 week cycle is repeated 3 or 4 times. In some embodiments, the subject is treated with a combination of an anti-PD-1 antibody and an anti-CTLA-4 antibody every 3 weeks for a total of 12 weeks and 3 twelve-week cycles are performed. In embodiments, the subject is treated with a combination of an anti-PD-1 antibody and an anti-CTLA-4 antibody every 3 weeks for a total of 12 weeks and 4 twelve-week cycles are performed. In embodiments, a subject is treated with the anti-PD1 antibody for 12 twelve-week cycles.

In certain embodiments, the administration of an anti-PD-1 antibody and an anti-CTLA-4 antibody is followed by an anti-PD-1 antibody monotherapy. In some embodiments, the antibody monotherapy after the combination therapy of an anti-PD-1 antibody and an anti-CTLA-4 antibody comprises administering an anti-PD-1 antibody at a dose of about 1 mg/kg body weight, about 2 mg/kg body weight, about 3 mg/kg body weight, about 4 mg/kg body weight, about 5 mg/kg body weight, about 6 mg/kg body weight, about 7 mg/kg body weight, about 8 mg/kg body weight, about 9 mg/kg body weight, or about 10 mg/kg body weight. In some embodiments, the anti-PD-1 monotherapy provided after the combination therapy of an anti-PD-1 antibody and an anti-CTLA-4 antibody is administered once about every 1, 2, 3, or 4 weeks. In a certain embodiment, the anti-PD-1 antibody monotherapy provided after the combination therapy of an anti-PD-1 antibody and an anti-CTLA-4 antibody is administered at a dose of about 3 mg/kg body weight once every 2 weeks.

In other embodiments, the anti-PD-1 antibody is administered at 3 mg/kg once every 3 weeks and the anti-CTLA-4 antibody is administered at 1 mg/kg once every 3 weeks. In certain embodiments, the anti-PD-1 antibody and the anti-CTLA-4 antibody are administered in combination for one dose each, two doses for each, three doses for each, four doses for each, five doses for each, six doses for each, seven doses for each, eight doses for each, nine doses for each, or ten doses for each. In a particular embodiment, the anti-PD-1 antibody and the anti-CTLA-4 antibody are administered in combination for four doses for each. In certain embodiments, the subject is administered, prior to and/or after the combination therapy of the anti-PD-1 antibody and the anti-CTLA-4 antibody, an anti-PD-1 antibody at a dose of 3 mg/kg for once every 2 weeks. In a particular embodiment, the subject afflicted with a colorectal cancer with MSI-H is treated with an initial stage (e.g., an anti-PD-1 antibody monotherapy, e.g., nivolumab at a dose of 3 mg/kg once every two weeks), a combination stage (e.g., an anti-PD-1 antibody and an anti-CTLA-4 antibody combination, e.g., nivolumab at a dose of 3 mg/kg once every three weeks and ipilimumab at a dose of 1 mg/kg once every week), and a final stage (e.g., an anti-PD-1 antibody monotherapy, e.g., nivolumab at a dose of 3 mg/kg once every two weeks).

Treatment can be continued as long as clinical benefit is observed or until unacceptable toxicity or disease progression occurs. In certain embodiments, the anti-PD-1 antibody can be administered at the dosage that has been shown to produce the highest efficacy as monotherapy in clinical trials, e.g., about 3 mg/kg of nivolumab administered once about every three weeks (Topalian et al., 2012 *N Engl J Med* 366:2443-54; Topalian et al., 2012 *Curr Opin Immunol* 24:207-12), or at a significantly lower dose, i.e., at a subtherapeutic dose.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Kits

Also within the scope of the present disclosure are kits comprising an anti-PD-1 antibody and another anti-cancer agent for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a tumor derived from a colorectal cancer, the kit comprising: (a) a dosage ranging from about 0.1 mg/kg to about 10 mg/kg of an anti-PD-1 antibody or antigen-binding portion thereof; and (b) instructions for using the anti-PD-1 antibody in any of the monotherapy methods disclosed herein. In other embodiments, the kit for treating a subject afflicted with a tumor derived from a colorectal cancer comprises: (a) a dosage ranging from about 0.1 mg/kg to about 10 mg/kg of an anti-PD-1 antibody or antigen-binding portion thereof; and (b) a dosage ranging from about 0.1 mg/kg to about 10 mg/kg of an anti-CTLA-4 antibody or antigen-binding portion thereof and (c) instructions for using the anti-PD-1 antibody and the anti-CTLA-4 antibody in any of the combination therapy methods disclosed herein. In certain embodiments, the anti-PD-1 antibody and the anti-CTLA-4 antibody can be co-packaged in unit dosage form. In certain embodiments for treating human patients, the kit comprises an anti-human PD-1 antibody disclosed herein, e.g., nivolumab, pembrolizumab, MEDI0608 (formerly AMP-514), AMP-224, or BGB-A317. In other embodiments, the kit comprises an anti-human CTLA-4 antibody disclosed herein, e.g., ipilimumab or tremelimumab.

The present disclosure is further illustrated by the following examples which should not be construed as further limiting. The contents of all references cited throughout this application are expressly incorporated herein by reference.

Cross-reference to earlier filed applications: the present application claims benefit to U.S. provisional application No. 62/345,662 filed Jun. 3, 2016, which is incorporated by reference herein by reference in its entirety.

EXAMPLES

Example 1

Clinical Case Study of Nivolumab±Ipilimumab in the Treatment of Patients with Metastatic Colorectal Cancer with and without High Microsatellite Instability Patients were eligible for inclusion in this study based upon the following criteria: 1) histologically confirmed colorectal cancer; 2) recurrent or metastatic disease measurable by Response Evaluation Criteria in Solid Tumors (RECIST) 1.1; 3) patient is an adult at least 18 years of age with Eastern Cooperative Oncology Group (ECOG) scores of 0-1; and 4) disease progression after ≥1 prior therapy regimen (for microsatellite instability-high patients) or after the latest treatment (for all patients) or intolerance or refusal to take chemotherapy. Patients were excluded from the study based upon the following criteria: 1) central nervous system involvement; 2) history of malignancy within 3 years; 3) active or history of autoimmune disease; 4) need for treatment with immunosuppressive medications including corticosteroids; or 5) prior treatments targeting T-cell costimulation or immune checkpoint pathways.

The colorectal cancer of patients was determined to be microsatellite instability-high (MSI-H) by polymerase chain reaction (PCR) if two or more markers showed instability out of 5 loci tested or if at least 30% of the markers showed instability when 5 or more loci were tested. The colorectal cancer of patients was also determined to be MSI-H by immunohistochemistry (IHC) if there was a loss of one or more markers.

Patients with 3L or later colon cancer that is non-MSI-H and with an ECOG performance status of 0-1 were selected for inclusion in the microsatellite stable (MSS) cohort of patients. Selected MSS patients were administered 1 mg/kg nivolumab in combination with 1 mg/kg ipilimumab once every 3 weeks for a total of 4 doses, followed by 3 mg/kg nivolumab once every 2 weeks. Six or more weeks following this initial phase of treatment, MSS patients who tolerated the initial therapeutic regimen were split into two treatment groups. In one treatment group, 10 MSS patients were administered 1 mg/kg nivolumab in combination with 3 mg/kg ipilimumab once every 3 weeks for a total of 4 doses, followed by 3 mg/kg nivolumab once every 2 weeks. In a second treatment group, 10 MSS patients were administered 3 mg/kg nivolumab in combination with 1 mg/kg ipilimumab once every 3 weeks for a total of 4 doses, followed by 3 mg/kg once every 2 weeks. Collectively, these treatment groups served as the independent safety arm in MSS patients and informed the dose of nivolumab in combination with ipilimumab for use in MSI-H patients. FIG. 1 shows the overall study design for patients in the MSS cohort.

Figure 2:
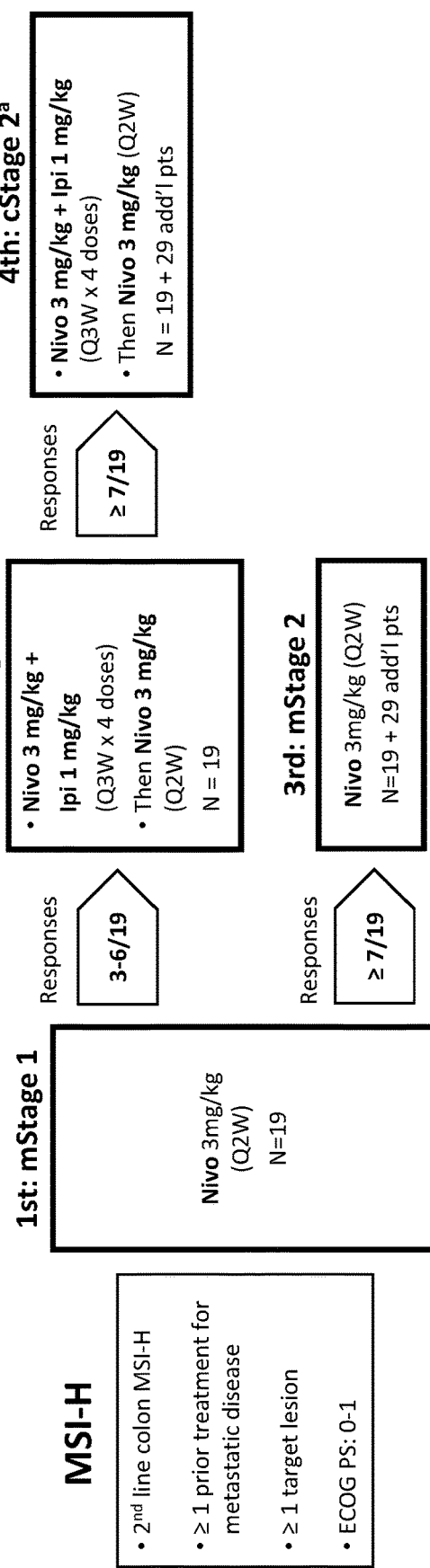
FIG. 2 shows a study schematic for microsatellite instability-high (MSI-H) colorectal cancer patients receiving 3 mg/kg nivolumab monotherapy or 3 mg/kg nivolumab in combination with 1 mg/kg ipilimumab.

Patients with $2^{nd}$ MSI-H colon cancer who had received at least 1 prior treatment for metastatic disease, who had at least 1 target lesion, and who had an ECOG performance status of 0-1 were selected for inclusion in the MSI-H cohort of patients. Nineteen MSI-H patients were administered 3 mg/kg nivolumab once every 2 weeks in an initial monotherapy stage of treatment (mStage 1). Certain MSI-H patients exhibiting positive responses were then selected for inclusion in a combination therapy stage of treatment (cStage 1). Nineteen of these MSI-H patients were then administered 3 mg/kg nivolumab in combination with 1 mg/kg ipilimumab once every 3 weeks for a total of 4 doses, followed by 3 mg/kg nivolumab once every two weeks in cStage 1. A number of patients with positive responses from the cStage 1 are currently being enrolled in a second stage of combination therapy (cStage 2). In cStage 2, 48 patients (19 patients from cStage 1 plus 29 additional patients) will receive 3 mg/kg nivolumab in combination with 1 mg/kg ipilimumab once every 3 weeks for a total of 4 doses, followed by 3 mg/kg nivolumab once every two weeks. A separate group of patients exhibiting positive responses in mStage 1 were selected for inclusion in a second stage of monotherapy (mStage 2). In mStage 2, 48 patients (19 patients from mStage 1 plus 29 new patients) were administered 3 mg/kg nivolumab once every 2 weeks. FIG. 2 shows the overall study design for patients in the MSI-H cohort.

The primary endpoint of this study was to determine the investigator-assessed objective response rate (ORR) using RECIST 1.1 in MSI-H patients. The secondary endpoint of this study was to determine the independent radiology review committee-assessed ORR in patients. Exploratory endpoints of this study included an assessment of safety and tolerability, progression-free survival (PFS), overall survival (OS), investigator-assessed ORR in MSS patients, and biomarkers.

The patient demographics collected for this study included median age, the number of patients under age 65, the number of male patients, the number of patients of a particular race, and the number of patients with an ECOG score of 0 or 1. Table 1 shows the demographics for MSI-H patients receiving 3 mg/kg nivolumab monotherapy compared to MSI-H patients receiving 3 mg/kg nivolumab in combination with 1 mg/kg ipilimumab. Table 2 also shows the demographics for MSS patients receiving 1 mg/kg nivolumab in combination with 3 mg/kg ipilimumab compared to MSS patients receiving 3 mg/kg nivolumab in combination with 1 mg/kg ipilimumab.

TABLE 2

Demographics for patients with MSI-H or MSS colorectal cancer.

| | MSI-H | | MSS | |
|---|---|---|---|---|
| | Nivo3 mg/kg (n = 70)$^a$ | Nivo 3 mg/kg + Ipi 1 mg/kg (n = 30)$^b$ | Nivo 1 mg/kg + Ipi 3 mg/kg (n = 10) | Nivo 3 mg/kg + Ipi 1 mg/kg (n = 10) |
| Median age, years (range) | 53 (26-79) | 60 (33-81) | 49 (35-65) | 52 (38-69) |
| Age, <65 years, n (%) | 54 (77.1) | 22 (73.3) | 9 (90.0) | 9 (90.0) |
| Male, n (%) | 42 (60.0) | 15 (50.0) | 7 (70.0) | 8 (80.0) |
| Race, n (%) | | | | |
| White | 61 (87.1) | 25 (83.3) | 10 (100) | 10 (100) |
| Black | 7 (10.0) | 1 (3.3) | 0 | 0 |
| Asian | 1 (1.4) | 2 (6.7) | 0 | 0 |
| Other | 1 (1.4) | 2 (6.7) | 0 | 0 |
| ECOG score, n (%)c | | | | |
| 0 | 30 (42.9) | 10 (33.3) | 4 (40.0) | 3 (30.0) |
| 1 | 39 (55.7) | 20 (66.7) | 6 (60.0) | 7 (70.0) |

ECOG, Eastern Cooperative Oncology Group.
$^a$mStages 1 and 2 combined;
$^b$cStages 1 and 2 combined;
cOne patient with an ECOG score of 1 at randomization had deteriorated to a score of 3 by the time of treatment initiation Data collected on disease characteristics and prior therapy included the number of patients with a particular disease stage at diagnosis, the number of patients with a particular mutation status, the number of patients receiving prior treatments, the number of patients receiving prior surgery, and the number of patients receiving prior radiotherapy. Table 3 shows the disease characteristics and prior therapy for MSI-H patients receiving 3 mg/kg nivolumab monotherapy compared to MSI-H patients receiving 3 mg/kg nivolumab in combination with 1 mg/kg ipilimumab. Table 3 also shows the disease characteristics and prior therapy for MSS patients receiving 1 mg/kg nivolumab in combination with 3 mg/kg ipilimumab compared to MSS patients receiving 3 mg/kg nivolumab in combination with 1 mg/kg ipilimumab.

TABLE 3

Disease characteristics and prior therapy for patients with MSI-H or MSS colorectal cancer.

| | MSI-H | | MSS | |
|---|---|---|---|---|
| | Nivolumab 3 mg/kg (n = 70)$^a$ | Nivolumab 3 mg/kg + Ipilimumab 1 mg/kg (n = 30)$^b$ | Nivolumab 1 mg/kg + Ipilimumab 3 mg/kg (n = 10) | Nivolumab 3 mg/kg + Ipilimumab 1 mg/kg (n = 10) |
| Disease stage at diagnosis, n (%) | | | | |
| I-II | 15 (21.4) | 2 (6.7) | 1 (10.0) | 1 (10.0) |
| III-IV | 54 (77.1) | 28 (93.3) | 9 (90.0) | 9 (90.0) |
| Mutation status, n % | | | | |
| KRAS/BRAF wild type | 26 (37.1) | 6 (20.0) | 2 (20.0) | 5 (50.0) |

TABLE 3-continued

Disease characteristics and prior therapy for patients with MSI-H or MSS colorectal cancer.

| | MSI-H | | MSS | |
|---|---|---|---|---|
| | Nivolumab 3 mg/kg (n = 70)$^a$ | Nivolumab 3 mg/kg + Ipilimumab 1 mg/kg (n = 30)$^b$ | Nivolumab 1 mg/kg + Ipilimumab 3 mg/kg (n = 10) | Nivolumab 3 mg/kg + Ipilimumab 1 mg/kg (n = 10) |
| BRAF mutated | 11 (15.7) | 6 (20.0) | 0 | 0 |
| KRAS mutated | 23 (32.9) | 14 (46.7) | 6 (60.0) | 3 (30.0) |
| Unknown | 10 (14.3) | 4 (13.3) | 2 (20.0) | 2 (20.0) |
| Prior treatments, n (%) | | | | |
| 1 | 9 (12.9) | 2 (6.7) | — | — |
| 2 | 21 (30.0) | 15 (50.0) | — | — |
| ≥3 | 39 (55.7) | 13 (43.3) | — | — |
| Prior surgery, n (%) | 70 (100) | 30 (100) | — | — |
| Prior radiotherapy, n (%) | 26 (37.1) | 7 (23.3) | — | — |

$^a$mStages 1 and 2 combined;
$^b$cStages 1 and 2 combined

Data regarding the dispositions of MSI-H patients collected in this study included the number of patients continuing treatment, the number of patients not continuing treatment, and the number of patients not continuing treatment due to disease progression, study drug toxicity, withdrawal of consent or other reasons, or for unreported reasons. Table 4 shows the patient dispositions for MSI-H patients receiving 3 mg/kg nivolumab monotherapy compared to MSI-H patients receiving 3 mg/kg nivolumab in combination with 1 mg/kg ipilimumab.

TABLE 4

MSI-H patient disposition.

| | MSI-H | |
|---|---|---|
| | Nivolumab 3 mg/kg (n = 70) | Nivolumab 3 mg/kg + Ipilimumab 1 mg/kg (n = 30) |
| Continuing treatment, n (%) | 47 (67.1) | 18 (60.0) |
| Not continuing treatment, n (%) | 23 (32.9) | 12 (40.0) |
| Reasons for not continuing, n (%) | | |
| Disease progression | 19 (27.1) | 6 (20.0) |
| Study drug toxicity | 2 (2.9) | 4 (13.3) |
| Withdrew consent/Other | 1 (1.4) | 1 (3.3) |
| Not reported | 1 (1.4) | 1 (3.3) |

Figure 3:
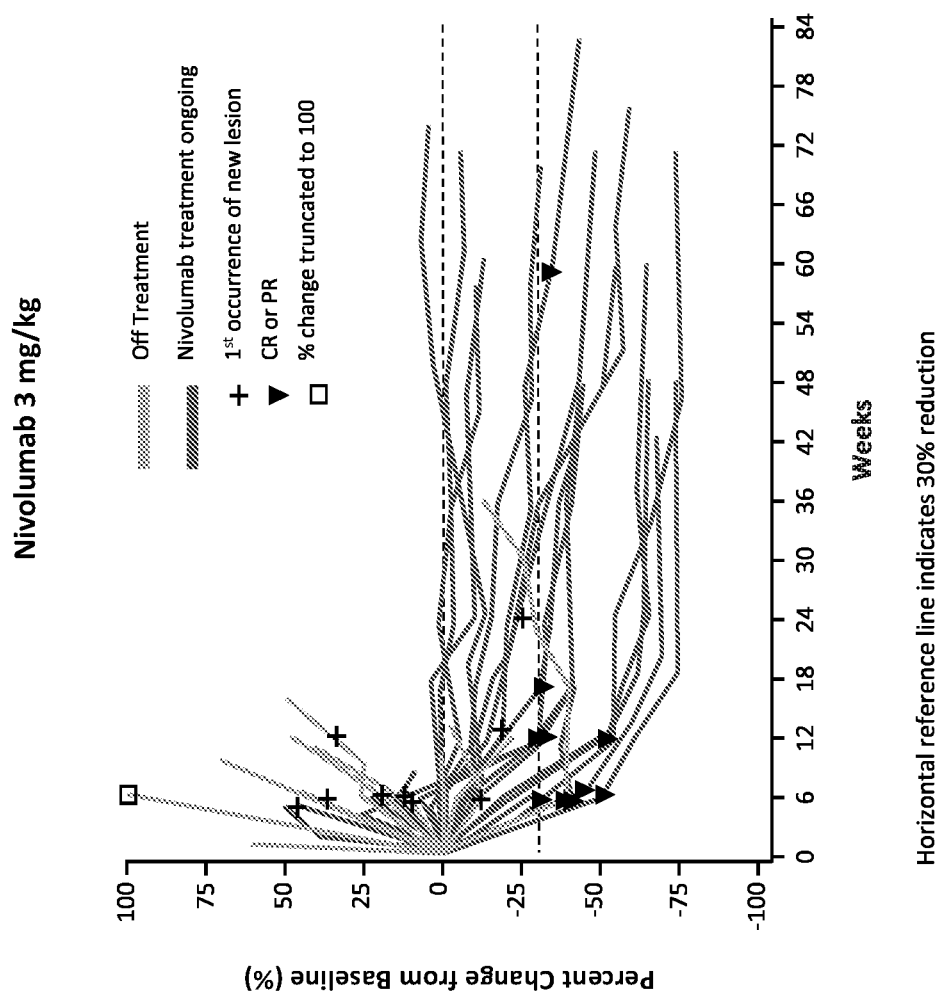
FIG. 3 shows the investigator-assessed objective responses of MSI-H colorectal cancer patients receiving 3 mg/kg nivolumab monotherapy.

The investigator-assessed best overall response in MSI-H patients receiving 3 mg/kg nivolumab monotherapy was determined by the objective response rate, the median time to response, and the median duration of response. As shown in Table 5, 12 out of 47 patients (25.5%) exhibited objective responses to 3 mg/kg nivolumab monotherapy, with the median time to response occurring at 2.12 months following treatment. FIG. 3 shows the percent change from baseline for individual patients receiving 3 mg/kg nivolumab monotherapy.

TABLE 5

Investigator-assessed best overall response in MSI-H patients receiving nivolumab monotherapy.

|  | Nivolumab 3 mg/kg (n = 47)[a] |
|---|---|
| Objective response rate, n (%) | 12/47 (25.5) |
| (95% exact CI) | (15.4, 38.1) |
| Complete response | 0 |
| Partial response | 12 (25.5) |
| Stable disease | 14 (29.8) |
| Progressive disease | 17 (36.2) |
| Unable to determine | 4 (8.5) |
| Median time to response, mo (range) | 2.12 (1.3-13.6) |
| Median duration of response, mo (range) | NE (0.0[b]-15.2[b]) |

[a]Patients with ≥12 weeks of follow-up
[b]Includes censored observations

Figure 4:
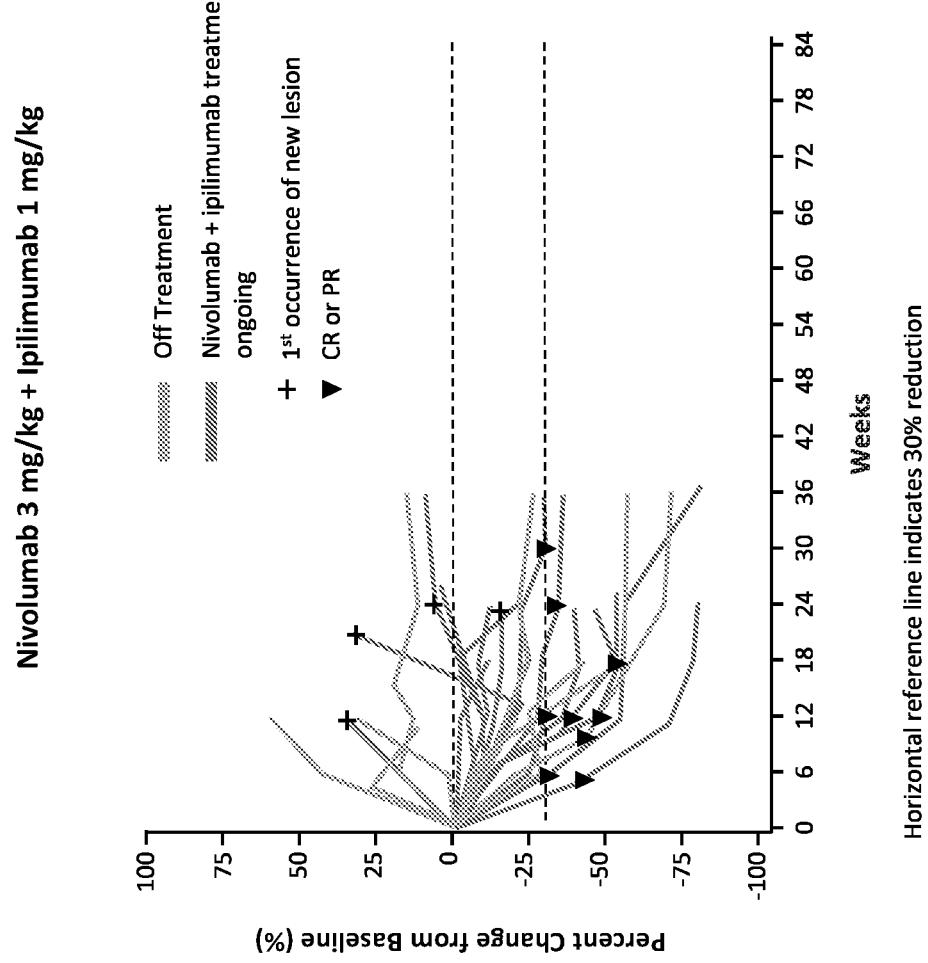
FIG. 4 shows the investigator-assessed objective responses of MSI-H colorectal cancer patients receiving 3 mg/kg nivolumab in combination with 1 mg/kg ipilimumab.

The investigator-assessed best overall response in MSI-H patients receiving 3 mg/kg nivolumab in combination with 1 mg/kg ipilimumab was determined by the objective response rate, the median time to response, and the median duration of response. As shown in Table 6, 9 out of 27 patients (33.3%) exhibited objective responses to treatment with 3 mg/kg nivolumab in combination with 1 mg/kg ipilimumab, with the median time to response occurring at 2.73 months following treatment. FIG. 4 shows the percent change from baseline for individual patients receiving 3 mg/kg nivolumab in combination with 1 mg/kg ipilimumab.

TABLE 6

Investigator-assessed best overall response in MSI-H patients receiving nivolumab in combination with ipilimumab.

|  | Nivolumab 3 mg/kg + Ipilimumab 1 mg/kg (n = 27)[a] |
|---|---|
| Objective response rate, n (%) | 9/27 (33.3) |
| (95% exact CI) | (18.6, 50.9) |
| Complete response | 0 |
| Partial response | 9 (33.3) |
| Stable disease | 14 (51.9) |
| Progressive disease | 3 (11.1) |
| Unable to determine | 0 |
| Median time to response, mo (range) | 2.73 (1.2-6.9) |
| Median duration of response, mo (range) | NE (NE-NE) |

[a]Patients with ≥12 weeks of follow-up
[b]Includes censored observations

Figure 5B:
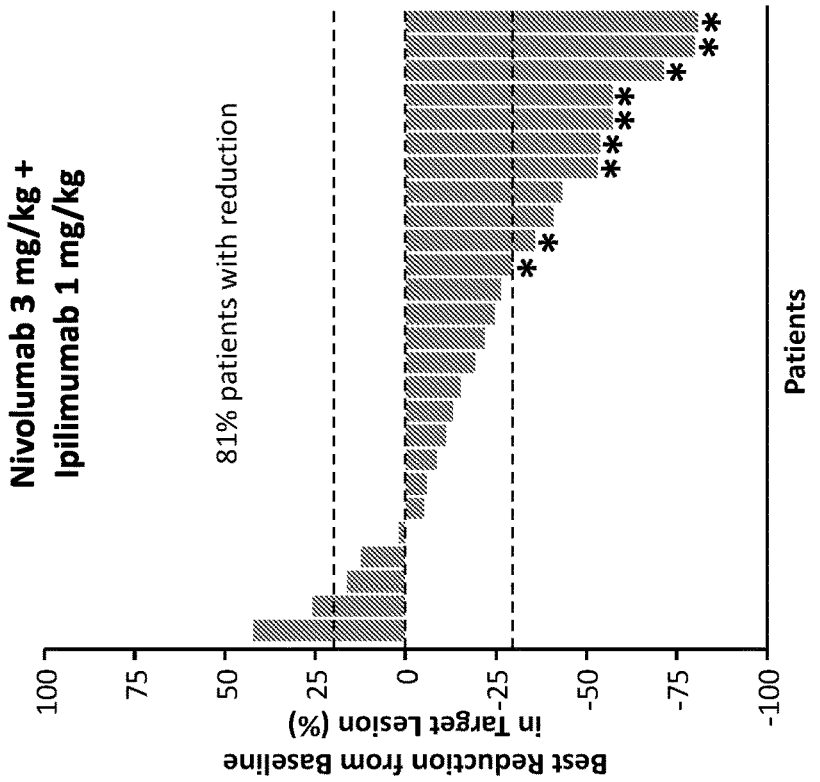
FIGS. 5A-5B show the best reduction in target lesion size for MSI-H colorectal cancer patients receiving 3 mg/kg nivolumab monotherapy (FIG. 5A) compared to MSI-H colorectal cancer patients receiving 3 mg/kg nivolumab in combination with 1 mg/kg ipilimumab (FIG. 5B).
Figure 5A:
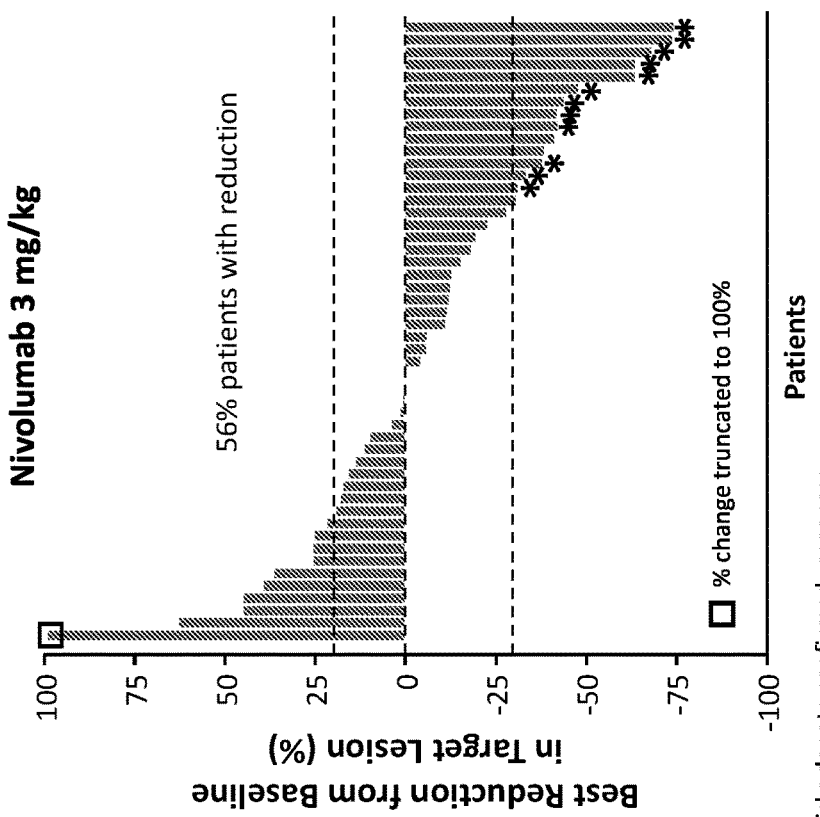

The best reduction in target lesion size for MSI-H patients receiving 3 mg/kg nivolumab monotherapy was compared to the best reduction in target lesion size for MSI-H patients receiving 3 mg/kg nivolumab in combination with 1 mg/kg ipilimumab. As shown in FIG. 5, 56% of patients receiving 3 mg/kg nivolumab monotherapy exhibited a reduction in target lesion size from baseline, while 81% of patients receiving 3 mg/kg nivolumab in combination with 1 mg/kg ipilimumab exhibited a reduction in target lesion size from baseline.

Figure 6:
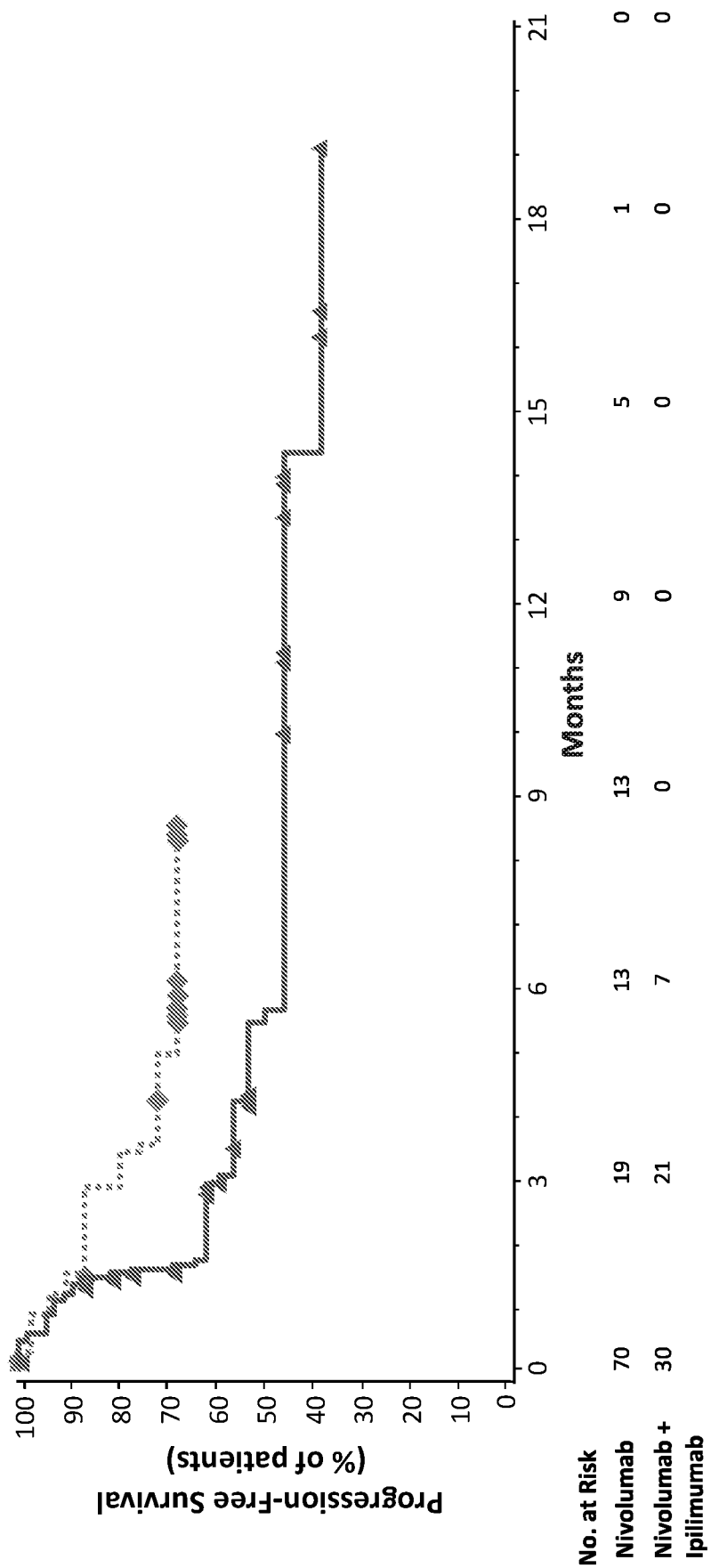
FIG. 6 shows the investigator-assessed progression-free survival of MSI-H colorectal cancer patients receiving 3 mg/kg nivolumab monotherapy or 3 mg/kg nivolumab in combination with 1 mg/kg ipilimumab.

Investigator-assessed PFS was measured at 6 months, 9 months, and 12 months for MSI-H patients receiving 3 mg/kg nivolumab monotherapy and at 6 months for MSI-H patients receiving 3 mg/kg nivolumab in combination with 1 mg/kg ipilimumab. As shown in Table 7, 45.9% of patients receiving 3 mg/kg nivolumab monotherapy exhibited progression-free survival at 6 months, while 66.6% of patients receiving 3 mg/kg nivolumab in combination with 1 mg/kg ipilimumab exhibited progression-free survival at 6 months. FIG. 6 shows the percentage of patients exhibiting progression-free survival for those receiving 3 mg/kg nivolumab monotherapy compared to those receiving 3 mg/kg nivolumab in combination with 1 mg/kg ipilimumab.

TABLE 7

Investigator-assessed progression-free survival in MSI-H patients.

| PFS rate, % (95% CI) | Nivolumab 3 mg/kg (n = 70) | Nivo 3 mg/kg + Ipilimumab 1 mg/kg (n = 30) |
|---|---|---|
| 6 mo | 45.9 (29.8, 60.7) | 66.6 (45.5, 81.1) |
| mo | 45.9 (29.8, 60.7) | NE |
| 12 mo | 45.9 (29.8, 60.7) | NE |
| Median PFS, mo (95% CI) | 5.3 (1.5, NE) | NE (3.4, NE) |

Figure 7:
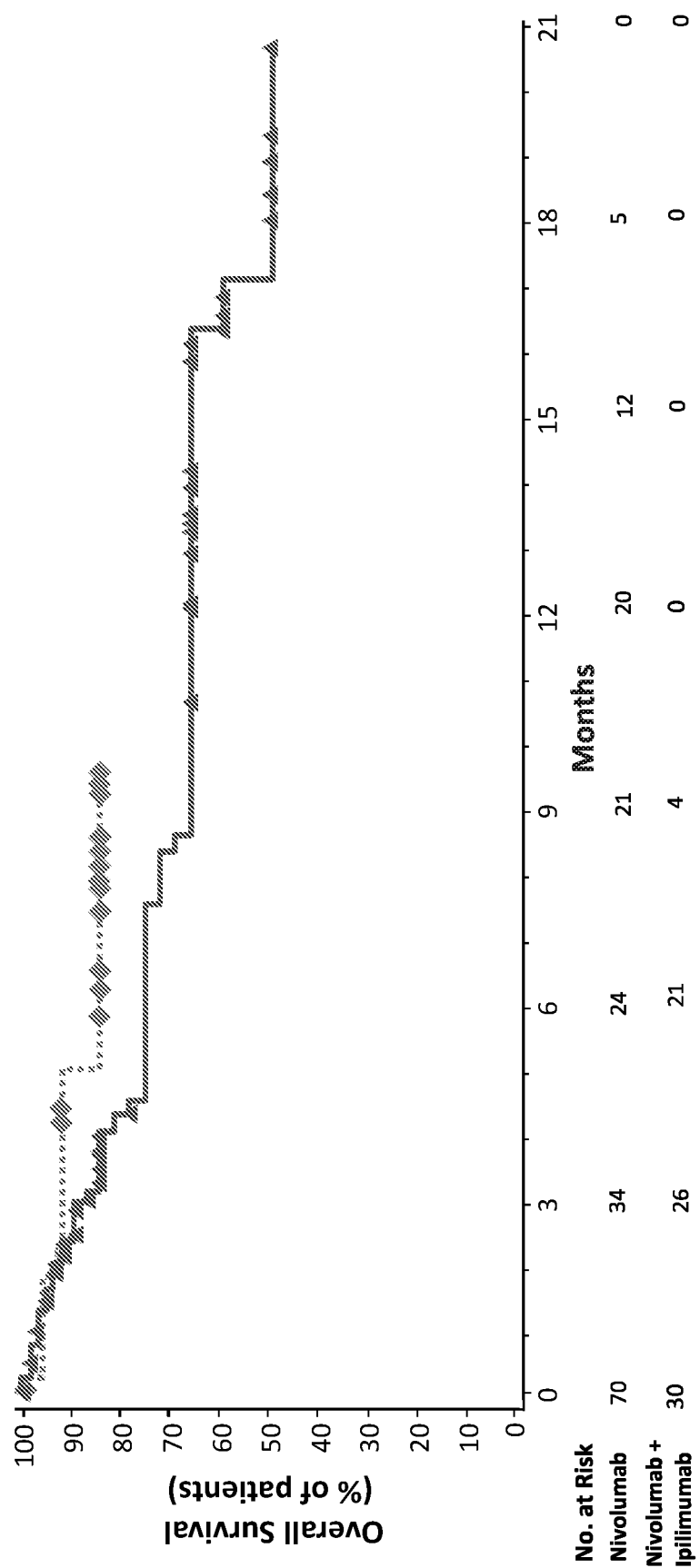
FIG. 7 shows the overall survival of MSI-H colorectal cancer patients receiving 3 mg/kg nivolumab monotherapy or 3 mg/kg nivolumab in combination with 1 mg/kg ipilimumab.

OS was measured at 6 months, 9 months, and 12 months for MSI-H patients receiving 3 mg/kg nivolumab monotherapy and at 6 months and 9 months for MSI-H patients receiving 3 mg/kg nivolumab in combination with 1 mg/kg ipilimumab. As shown in Table 8, 75.0% of patients receiving 3 mg/kg nivolumab monotherapy exhibited progression-free survival at 6 months, while 85.1% of patients receiving 3 mg/kg nivolumab in combination with 1 mg/kg ipilimumab exhibited progression-free survival at 6 months. At 9 months, 65.6% of patients receiving 3 mg/kg nivolumab monotherapy exhibited progression-free survival, while 85.1% of patients receiving 3 mg/kg nivolumab in combination with 1 mg/kg ipilimumab exhibited progression free survival. FIG. 7 shows the percentage of patients exhibiting overall survival for those receiving 3 mg/kg nivolumab monotherapy compared to those receiving 3 mg/kg nivolumab in combination with 1 mg/kg ipilimumab.

TABLE 8

Overall survival in MSI-H patients.

| OS rate, % (95% CI) | Nivolumab 3 mg/kg (n = 70) | Nivo 3 mg/kg + Ipilimumab 1 mg/kg (n = 30) |
|---|---|---|
| 6 mo | 75.0 (58.5, 85.7) | 85.1 (65.0, 94.2) |
| mo | 65.6 (48.0, 78.6) | 85.1 (65.0, 94.2) |
| 12 mo | 65.6 (48.0, 78.6) | NE |
| Median OS, mo (95% CI) | 17.1 (8.6, NE) | NE (NE, NE) |

The efficacy of treatment in MSS colorectal cancer patients was measured by ORR, PFS, and OS. Table 9 shows a summary of efficacy data in MSS patients receiving 1 mg/kg nivolumab in combination with 3 mg/kg ipilimumab compared to MSS patients receiving 3 mg/kg nivolumab in combination with 1 mg/kg ipilimumab.

TABLE 9

Summary of efficacy in MSS colorectal cancer patients.

|  | Nivolumab 1 mg/kg + Ipilimumab 3 mg/kg (n = 10) | Nivolumab 3 mg/kg + Ipilimumab 1 mg/kg (n = 10) |
|---|---|---|
| ORR, n (%) | 1 (10) | 0 |
| Median PFS, mo (95% CI) | 2.28 (0.62, 4.40) | 1.31 (0.89, 1.71) |
| Median OS, mo (95% CI) | 11.53 (0.62, NE) | 3.73 (1.22, 5.62) |

Treatment-related adverse events that were observed in ≥15% of MSI-H colorectal cancer patients included fatigue, diarrhea, pruritus, nausea, pyrexia, and vomiting. Table 10 shows the treatment-related adverse events in ≥15% of MSI-H patients receiving 3 mg/kg nivolumab compared to MSI-H patients receiving 3 mg/kg nivolumab in combination with 1 mg/kg ipilimumab.

TABLE 10

Treatment-related adverse events in ≥15% of MSI-H patients.

| Event, n (%) | Nivolumab 3 mg/kg (n = 70) | | Nivolumab 3 mg/kg + Ipilimumab 1 mg/kg (n = 30) | |
|---|---|---|---|---|
| | Any grade | Grade 3-4 | Any grade | Grade 3-4 |
| Any event | 41 (58.6)[a] | 10 (14.3) | 25 (83.3) | 8 (26.7) |
| Fatigue | 13 (18.6) | 1 (1.4) | 6 (20.0) | 0 |
| Diarrhea | 10 (14.3) | 1 (1.4) | 13 (43.3) | 0 |
| Pruritus | 8 (11.4) | 0 | 5 (16.7) | 1 (3.3) |
| Nausea | 5 (7.1) | 0 | 6 (20.0) | 0 |
| Pyrexia | 3 (4.3) | 0 | 7 (23.3) | 0 |
| Vomiting | 1 (1.4) | 0 | 3 (10.0) | 0 |
| Any event leading to discontinuation | 4 (5.7) | 2 (2.9) | 4 (13.3) | 4 (13.3) |

[a]One Grade 5 event of sudden death

Treatment-related adverse events that were observed in ≥15% of MSS colorectal cancer patients included diarrhea, asthenia, nausea, pyrexia, vomiting, fatigue, dry skin, and cough.

The results of this study demonstrated the encouraging activity of nivolumab monotherapy in patients with MSI-H status. The combination of nivolumab and ipilimumab also demonstrated promising preliminary activity. The results of this study showed that responses to nivolumab monotherapy and to nivolumab+ipilimumab combination therapy were durable. Nivolumab and the combination of nivolumab and ipilimumab demonstrated tolerable safety profiles in relation to the clinical benefit and were consistent with observations in other solid tumors. Such results are encouraging and support the continued evaluation of nivolumab monotherapy and nivolumab+ipilimumab combination therapy in patients with MSI-H metastatic colorectal cancer and potentially other tumors with mismatch repair defects.

Example 2

Extended Clinical Case Study of Nivolumab+Ipilimumab in the Treatment of Patients with Deficient DNA Mismatch Repair/High Microsatellite Instability Metastatic Colorectal Cancer Further to the clinical case study described in Example 1, the efficacy and safety of nivolumab in combination with ipilimumab was investigated in an expanded population of patients with DNA mismatch repair-deficient/microsatellite instability-high (dMMR/MSI-H) metastatic colorectal cancer (mCRC) who had received a first treatment dose at least six months prior to the data cut-off. Patients were eligible for inclusion in this study based upon the following criteria: 1) histologically confirmed metastatic/recurrent colorectal cancer; 2) dMMR/MSI-H indicated by local laboratory; and 3) at least one prior line of therapy.

Figure 8:
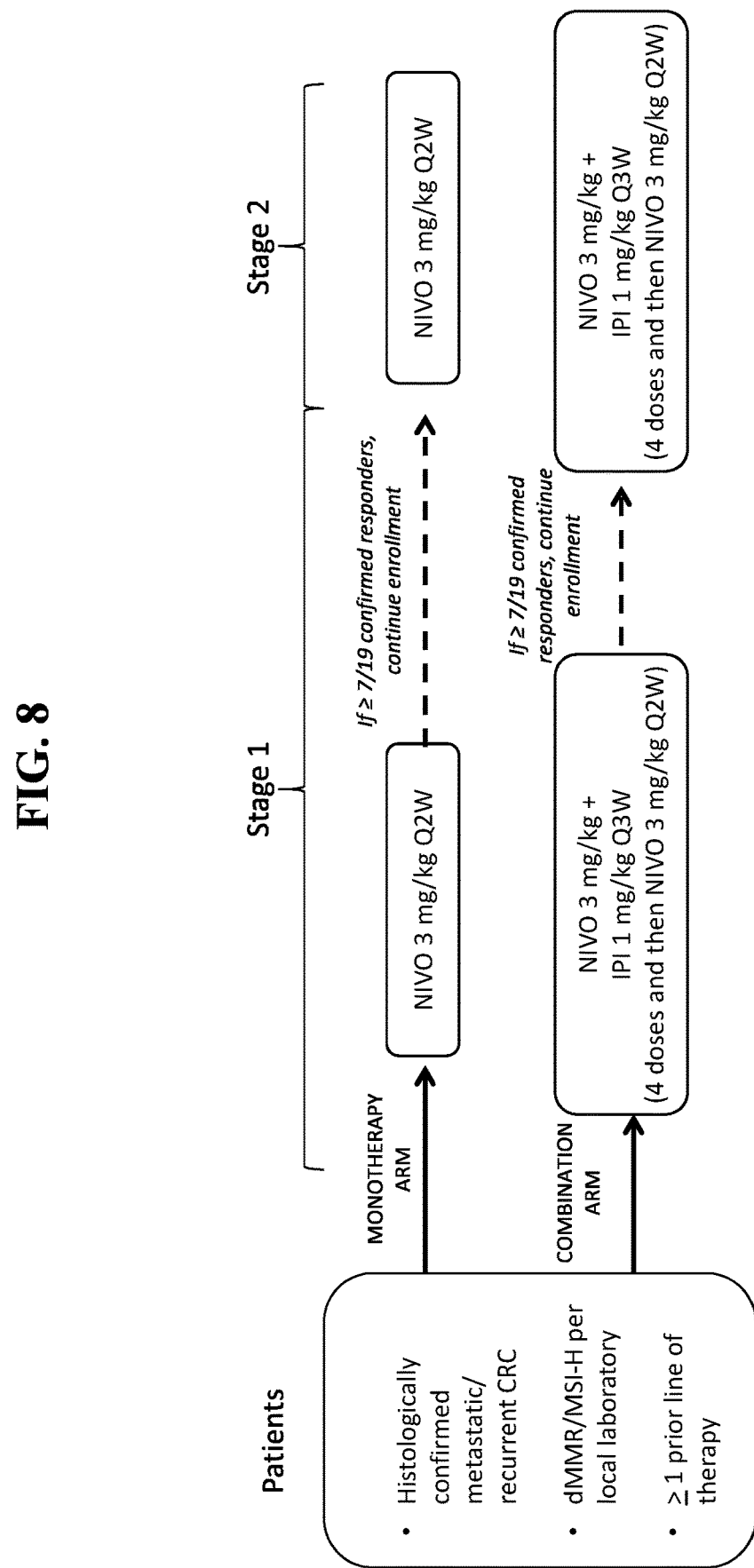
FIG. 8 shows a study schematic for DNA mismatch repair-deficient/microsatellite instability-high (dMMR/MSI-H) metastatic colorectal cancer patients receiving 3 mg/kg nivolumab monotherapy or 3 mg/kg nivolumab+1 mg/kg ipilimumab combination therapy.

FIG. 8 shows the overall study design for patients included in a monotherapy arm or combination therapy arm of treatment. Briefly, patients included in the monotherapy arm were administered 3 mg/kg nivolumab once every two weeks in Stage 1 of treatment. If there were at least seven out of nineteen confirmed responders, enrollment was continued for a secondary stage of treatment. In Stage 2 of treatment, patients were administered 3 mg/kg nivolumab once every two weeks. Patients included a separate combination arm were administered 3 mg/kg nivolumab in combination with 1 mg/kg ipilimumab once every three weeks for four doses, followed by 3 mg/kg nivolumab once every two weeks in Stage 1 of treatment. If there were at least seven out of nineteen confirmed responders, enrollment was continued for a secondary stage of treatment. In Stage 2 of treatment, patients were administered 3 mg/kg nivolumab in combination with 1 mg/kg ipilimumab once every three weeks for four doses, followed by 3 mg/kg nivolumab once every two weeks. Further details regarding the study design are described in Overman M et al., *J Clin Oncol.* 2017; 35: (suppl 4S; abstract 519) and Overman M et al., *Ann Oncol.* 2016; 27 (6): 149-206 (abstract 479P).

The primary endpoint of this study was to determine the investigator-assessed objective response rate (ORR) using RECIST 1.1. Other key endpoints included the determination of ORR by blinded independent central review (BICR) and assessments of progression-free survival (PFS), overall survival (OS), and safety. Tumor imaging assessments were performed every six weeks for 24 weeks and thereafter every 12 weeks until disease progression or discontinuation. Treatment beyond progression was permitted if the patient was determined by the investigator to be benefitting from and tolerating study therapy, and consent was provided by the patient.

Figure 9:
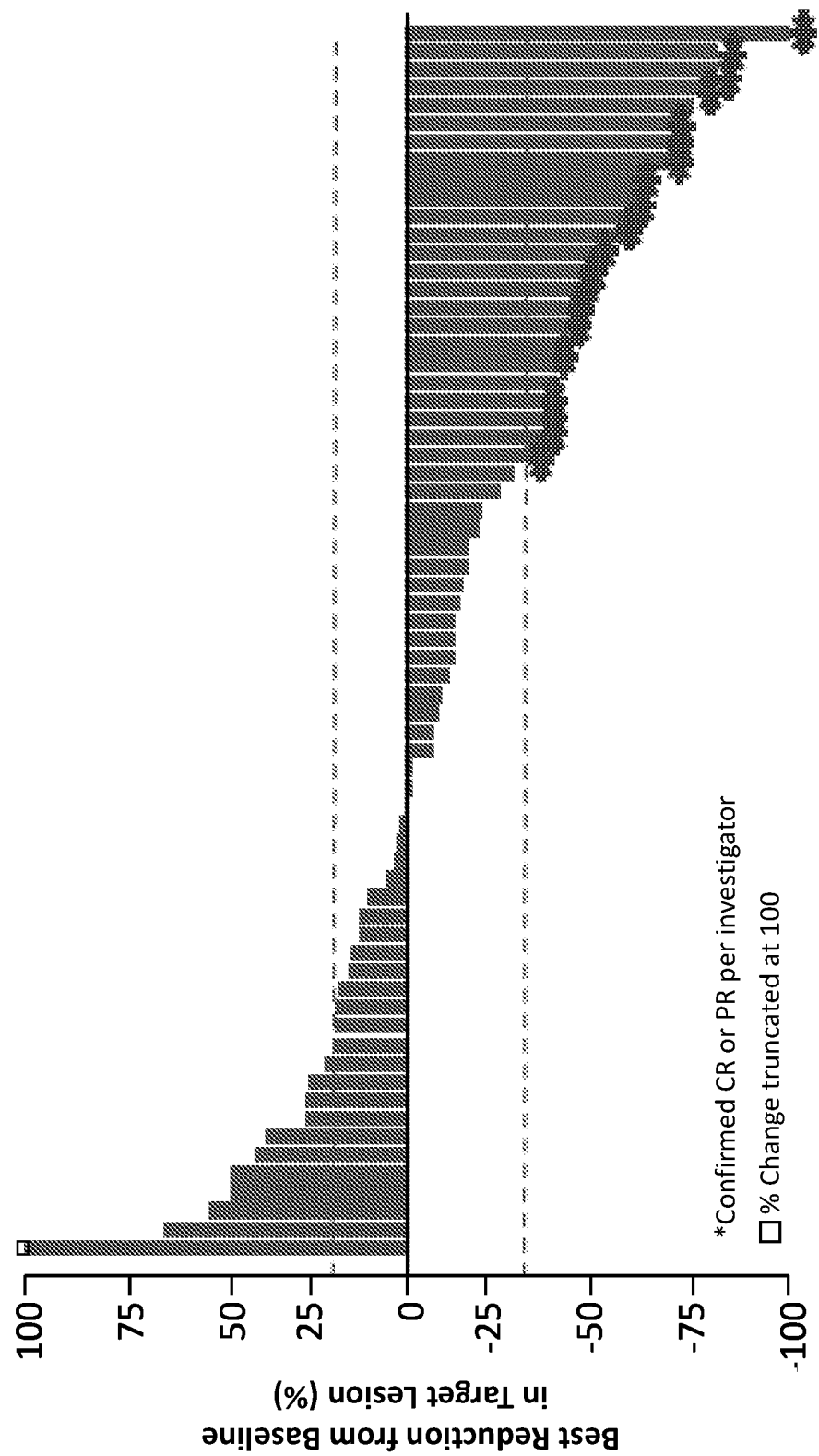
FIG. 9 shows the best reduction from baseline in target lesion size for dMMR/MSI-H metastatic colorectal cancer patients receiving nivolumab monotherapy in an extended clinical case study.

Investigator-assessed responses with nivolumab monotherapy were determined for 74 patients. Nivolumab monotherapy demonstrated durable responses, sustained disease control, and a 12-month overall survival (OS) rate of 74%. The objective response rate (ORR) in patients receiving nivolumab monotherapy was 31%, with a median time to response (TTR) of 2.8 months. A median duration of response (DOR) was not reached in patients receiving nivolumab monotherapy, with 83% (19/23) responses ongoing. As shown in FIG. 9, 62% of patients receiving nivolumab monotherapy had a reduction in tumor burden from baseline. Further details regarding the nivolumab monotherapy are provided in Overman M et al., J Clin Oncol. 2017; 35: (suppl 4S; abstract 519).

The patient demographics collected for this study included median age, the number of patients under age 65, the number of male patients, the number of patients of a particular race, the number of patients with an ECOG score of 0 or 1, the number of patients at a particular disease stage at initial diagnosis, the number of patients with a particular clinical history of Lynch syndrome, the number of patients with a particular BRAF or KRAS mutation status, the number of patients with tumor PD-L1 expression of ≥1% or <1% at baseline, the number of patients with a certain number of prior lines of therapy, and the number of patients with prior radiotherapy. Table 11 shows the baseline patient demographics and disease characteristics for 84 dMMR/MSI-H metastatic colorectal cancer patients receiving combination therapy with 3 mg/kg nivolumab+1 mg/kg ipilimumab.

TABLE 11

Baseline patient demographics and disease characteristics for patients receiving nivolumab + ipilimumab combination therapy.

| | dMMR/MSI-H (N = 84) |
|---|---|
| Age | |
| Median (range), years | 57 (21-81) |
| <65 years, n (%) | 61 (73) |
| Male, n (%) | 48 (57) |
| Race, n (%) | |
| White | 77 (92) |
| Black | 2 (2) |
| Asian | 3 (4) |
| Other | 2 (2) |
| ECOG performance status, n (%) | |
| 0 | 31 (37) |
| 1 | 53 (63) |
| Disease stage at initial diagnosis, n (%) | |
| I-II | 9 (11) |
| III | 33 (39) |
| IV | 42 (50) |
| Clinical history of Lynch syndrome, n (%) | |
| Yes | 27 (32) |
| No | 25 (30) |
| Unknown | 32 (38) |
| Mutation status, n (%) | |
| BRAF/KRAS wild type | 22 (26) |
| BRAF mutated | 21 (25) |
| KRAS mutated | 30 (36) |
| Tumor PD-L1 expression quantifiable at baseline, n (%) | |
| ≥1% | 16 (24) |
| <1% | 50 (76) |
| Prior lines of therapy, n (%) | |
| 0 | 1 (1) |
| 1 | 17 (20) |
| 2 | 31 (37) |
| 3 | 23 (27) |
| >4 | 12 (14) |
| Prior radiotherapy, n (%) | 17 (20) |

Data regarding the dispositions of dMMR/MSI-H metastatic colorectal cancer patients collected in this study included the number of doses received, the number of patients continuing treatment, the number of patients that discontinued treatment, and the number of patients discontinuing treatment for a particular reason. The median time from first dose to data cut-off was 8.6 months, with a range of 6.3-19.4 months. Table 12 shows the patient dispositions for 84 dMMR/MSI-H metastatic colorectal cancer patients receiving combination therapy with 3 mg/kg nivolumab+1 mg/kg ipilimumab.

TABLE 12

Patient disposition for dMMR/MSI-H metastatic colorectal cancer patients receiving nivolumab + ipilimumab combination therapy.

| | MMR/MSI-H (N = 84) |
|---|---|
| Number of doses received, median (SD) | 14.4 (10.8) |
| Continuing treatment, n (%) | 51 (61) |
| Discontinued treatment, n (%) | 33 (39) |

TABLE 12-continued

Patient disposition for dMMR/MSI-H metastatic colorectal cancer patients receiving nivolumab + ipilimumab combination therapy.

| | MMR/MSI-H (N = 84) |
|---|---|
| Reasons for discontinuing treatment, n (%) | |
| Disease progression | 15 (18) |
| Treatment-related adverse event | 11 (13) |
| Death | 1 (1) |
| Adverse event unrelated to study drug | 1 (1) |
| Lost to follow up | 1 (1) |
| Patient decision | 1 (1) |
| Not reported/other | 3 (4) |

SD, standard deviation

The investigator-assessed objective response rate (ORR), best overall response, number of patients with disease control for ≥12 weeks, median time to response (TTR), and median duration of response (DOR) were determined for dMMR/MSI-H metastatic colorectal cancer patients receiving nivolumab+ipilimumab combination therapy. The best overall response was determined by measuring the number of patients with complete remission, partial remission, stable disease, or progressive disease. As shown in Table 13, an investigator-assessed ORR was achieved in 55% of patients and the disease control rate (DCR) was 79%.

TABLE 13

Summary of response and disease control for dMMR/MSI-H metastatic colorectal cancer patients receiving nivolumab + ipilimumab combination therapy.

| | dMMR/MSI-H (N = 84) |
|---|---|
| ORR, n (%) | 46 (55) |
| [95%, CI] | [43.5, 65.7] |
| Best overall response, n (%) | |
| CR | 2 (2) |
| PR | 44 (52) |
| SD | 26 (31) |
| PD | 9 (11) |
| Not determined/reported | 3 (3) |
| Disease control for ≥12 weeks,[a] n (%) | 66 (79) |
| [95% CI] | [68.3, 86.8] |
| Median TTR, months (range) | 2.8 (1.1-14.0) |
| Median DOR, months, | NR |
| [95% CI] | [NR, NR] |

DOR, duration of response;
NR, not reached;
TTR, time to response;
[a]Patients with CR, PR, or SD for ≥12 weeks.

Figure 10:
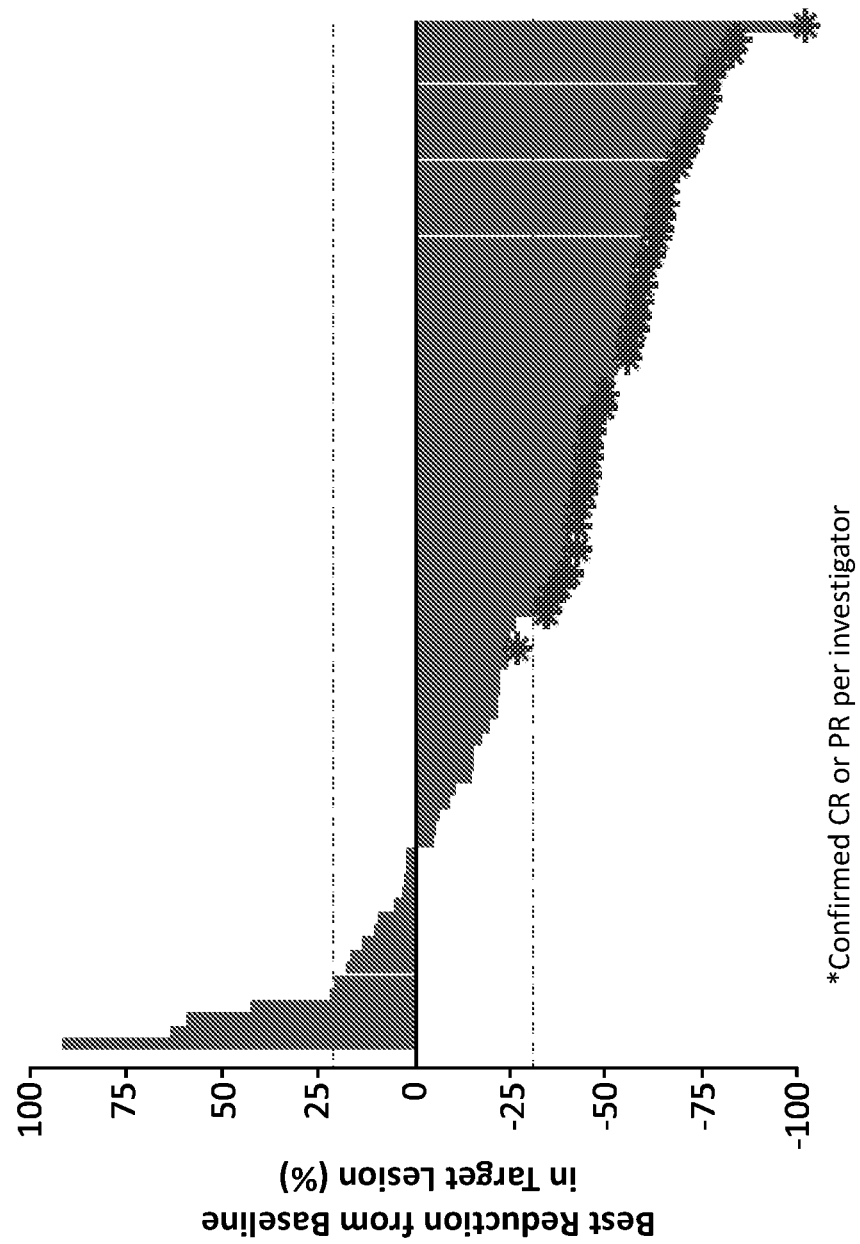
FIG. 10 shows the best reduction from baseline in target lesion size for dMMR/MSI-H metastatic colorectal cancer patients receiving nivolumab+ipilimumab combination therapy.
Figure 11:
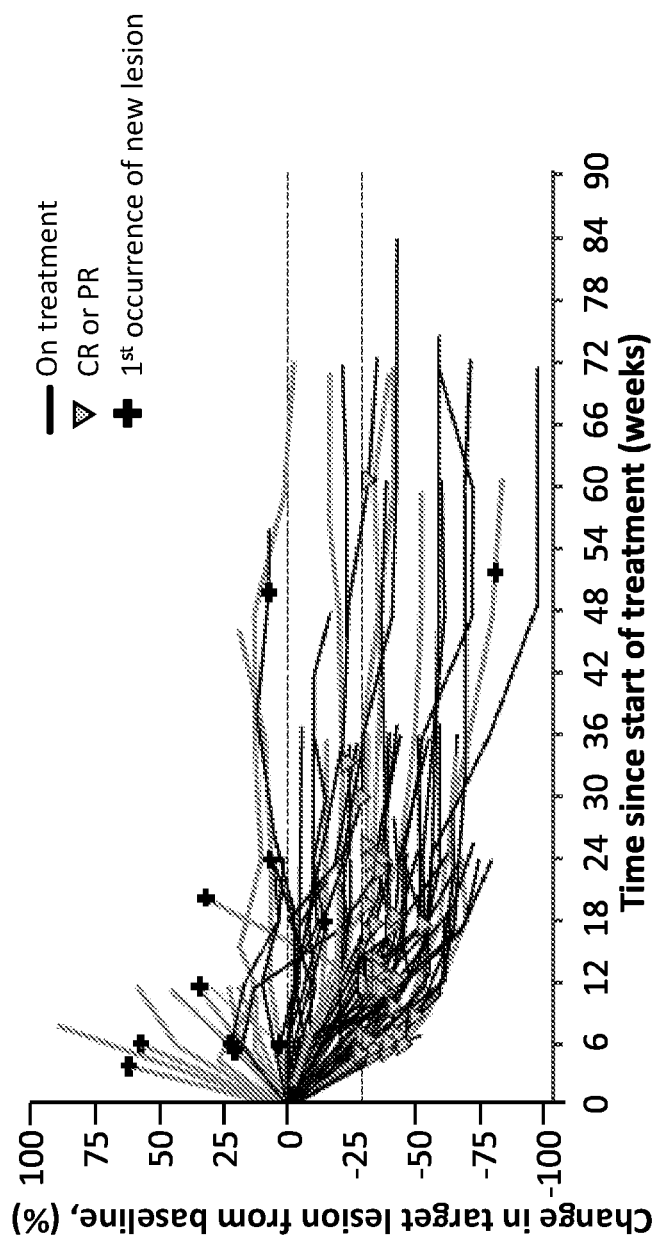
FIG. 11 shows the change in tumor burden over time for dMMR/MSI-H metastatic colorectal cancer patients receiving nivolumab+ipilimumab combination therapy.

The best reduction in target lesion size and change in tumor burden over time was determined for dMMR/MSI-H metastatic colorectal cancer patients receiving nivolumab+ipilimumab combination therapy. As shown in FIG. 10, 80% of patients had a reduction in tumor burden from baseline. The patient-specific characteristics of the change in tumor burden over time are shown in FIG. 11. At the time of data base cut-off, 85% (39/46) responses were ongoing.

Figure 12A:
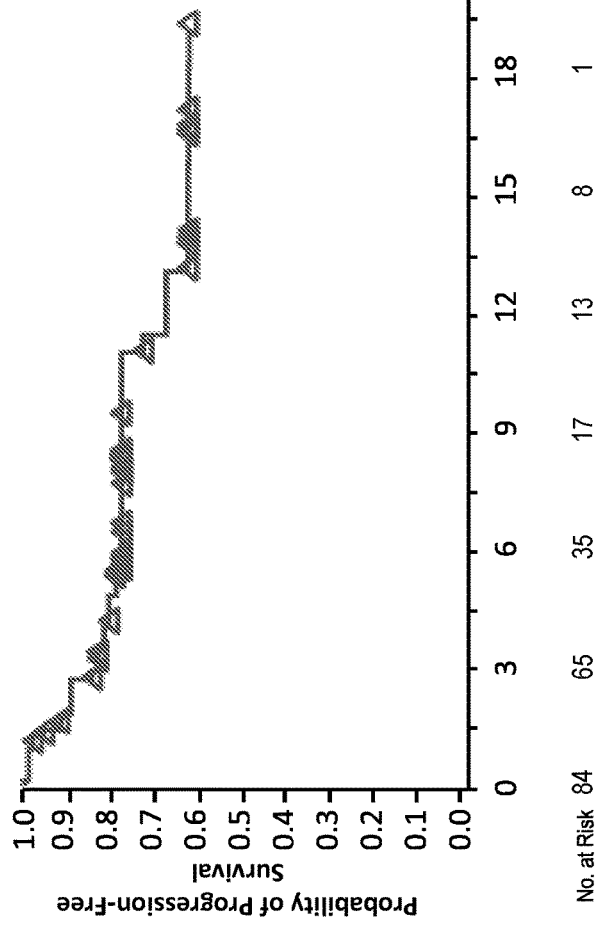
FIGS. 12A-12B show the progression-free survival (PFS) per investigator assessment (FIG. 12A) and overall survival (OS) per investigator assessment (FIG. 12B) for dMMR/MSI-H metastatic colorectal cancer patients receiving nivolumab+ipilimumab combination therapy.
Figure 12B:
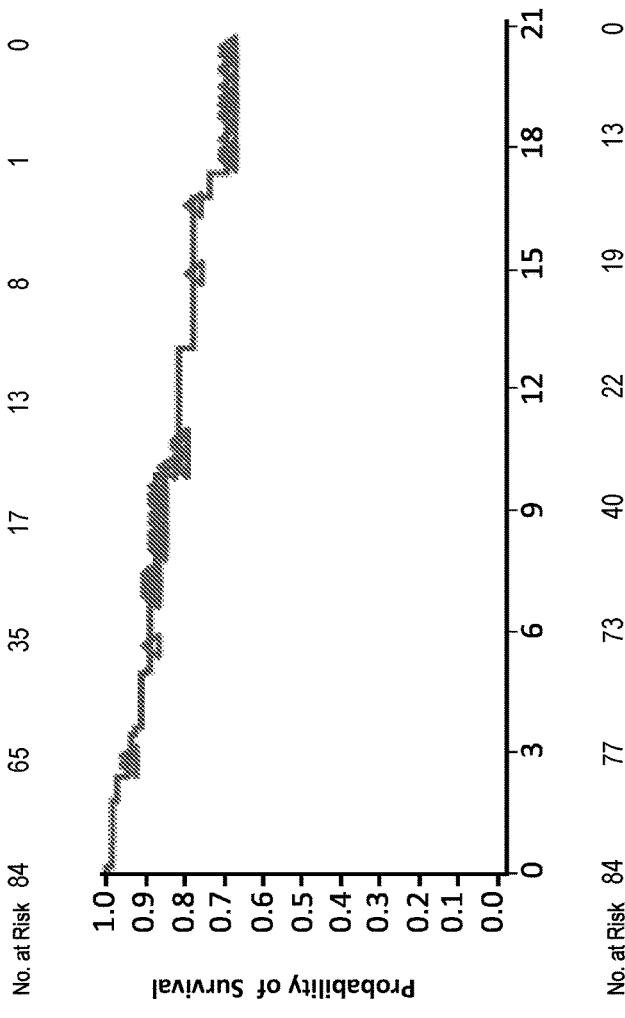

Progression-free survival (PFS) and overall survival (OS) were assessed for dMMR/MSI-H metastatic colorectal cancer patients receiving nivolumab+ipilimumab combination therapy. The median time from the first dose to death or the last known alive date was 8.7 months for these patients, with a range of 0.1 months to 20.1 months. As shown in FIG. 12A, the 9-month PFS rate was 77%, while the 6-month and 12-month PFS rates were also each 77% (66.5%, 85.1% at 95% CI). The median PFS in months had not been reached at the time of data cut-off (11.47, Not estimable at 95% CI). As shown in FIG. 12B, the 9-month OS rate was 88%, while the 6-month OS rate was 89% (80.2%, 94.2% at 95% CI) and the 12-month OS rate was 88% (78.1%, 93.1% at 95% CI). The median OS in months had not been reached at the time of data cut-off (Not estimable, not estimable at 95% CI).

Treatment-related adverse events (TRAEs) that were observed in dMMR/MSI-H metastatic colorectal cancer patients receiving nivolumab+ipilimumab combination therapy included diarrhea, fatigue, aspartate aminotransferase increase, pyrexia, pruritis, alanine aminotransferase increase, nausea, hyperthyroidism, and hypothyroidism. All adverse events were manageable, with Grade ¾ TRAEs reported in 29% of patients. No treatment-related deaths were reported.

The results of this study demonstrated that combination therapy with nivolumab+ipilimumab provided durable responses, sustained disease control, and encouraging survival data in pretreated patients with dMMR/MSI-H metastatic colorectal cancer. Combination therapy with nivolumab+ipilimumab also demonstrated a manageable safety profile. Such results are encouraging and support the continued evaluation of combination therapy with nivolumab+ipilimumab in patients with dMMR/MSI-H metastatic colorectal cancer and potentially other tumors.

What is claimed is:

1. A method of treating a subject afflicted with a tumor derived from a colorectal cancer, comprising administering to the subject:
   (i) an anti-PD-1 antibody, and
   (ii) an anti-CTLA-4 antibody;
   wherein the tumor is a colon cancer or a rectal cancer; and
   wherein the tumor exhibits a high degree of microsatellite instability (MSI-H).

2. The method of claim 1, wherein the tumor exhibits one or more characteristics selected from the group consisting of:
   (a) the tumor comprises a germline alteration in at least two DNA mismatch repair genes (MMR genes);
   (b) the tumor comprises a germline alteration in at least 30% of five or more MMR genes;
   (c) at least one protein encoded by DNA MMR genes is not detected in the tumor; and
   (d) any combination thereof.

3. The method of claim 2, wherein the DNA MMR genes comprise MSH2, MLH1, MSH6, PMS2, PMS1, or any combination thereof.

4. The method of claim 1, wherein:
   (i) the subject exhibits a progression-free survival of at least about one month after the administration, or
   (ii) the subject exhibits an overall survival of at least about one month after the administration.

5. The method of claim 1, wherein the anti-PD-1 antibody is nivolumab or pembrolizumab.

6. The method of claim 1, wherein the anti-CTLA-4 antibody is administered at a dose ranging from at least about 0.1 mg/kg to at least about 10.0 mg/kg body weight once about every 1, 2, 3, or 4 weeks.

7. The method of claim 1, wherein the anti-CTLA-4 antibody is ipilimumab or tremelimumab.

8. The method of claim 1, wherein the anti-PD-1 antibody is administered at a dose ranging from at least about 0.1 mg/kg to at least about 10.0 mg/kg body weight once about every 1, 2, 3, or 4 weeks.

9. The method of claim 1, wherein:
   (i) the anti-PD-1 antibody is administered at a dose of about 1 mg/kg body weight and the anti-CTLA-4 antibody is administered at a dose of about 1 mg/kg body weight;
   (ii) the anti-PD-1 antibody is administered at a dose of about 1 mg/kg body weight and the anti-CTLA-4 antibody is administered at a dose of about 3 mg/kg body weight;
   (iii) the anti-PD-1 antibody is administered at a dose of about 3 mg/kg body weight and the anti-CTLA-4 antibody is administered at a dose of about 1 mg/kg body weight; or
   (iv) the anti-PD-1 antibody is administered at a dose of about 3 mg/kg body weight and the anti-CTLA-4 antibody is administered at a dose of about 3 mg/kg body weight.

10. The method of claim 9, wherein the administration of the anti-PD-1 antibody and the anti-CTLA-4 antibody is followed by an anti-PD-1 antibody monotherapy.

11. The method of claim 1, wherein the anti-PD-1 antibody is administered at a dose of about 3 mg/kg body weight and the anti-CTLA-4 antibody is administered at a dose of about 1 mg/kg body weight once about every 3 weeks for a total of 12 weeks.

12. The method of claim 11, wherein the administration of the anti-PD-1 antibody and the anti-CTLA-4 antibody is followed by an anti-PD-1 antibody monotherapy.

13. The method of claim 12, wherein the anti-PD-1 antibody monotherapy is administered once about every 2 weeks.

14. The method of claim 12, wherein the anti-PD-1 antibody monotherapy is administered at a dose of about 3 mg/kg once about every 2 weeks.

15. The method of claim 12, wherein the anti-PD-1 antibody monotherapy is administered as a flat dose.

16. The method of claim 12, wherein the anti-PD-1 antibody monotherapy is administered at a flat dose of about 240 mg once about every 2 weeks.

17. The method of claim 16, wherein the anti-PD-1 antibody is nivolumab.

18. The method of claim 17, wherein the anti-CTLA-4 antibody is ipilimumab.

* * * * *